United States Patent
Marinier et al.

(10) Patent No.: US 9,429,566 B2
(45) Date of Patent: Aug. 30, 2016

(54) ASSAY FOR INHIBITORS OF CIP/KIP PROTEIN DEGRADATION

(71) Applicant: UNIVERSITE DE MONTREAL, Montreal (CA)

(72) Inventors: Anne Marinier, Kirkland (CA); Sylvain Meloche, Montreal (CA); Benoit Pelletier, Chambly (CA)

(73) Assignee: UNIVERSITÉ DE MONTRÉAL, Montreal (CA)

( * ) Notice: Subject to any disclaimer, the term of this patent is extended or adjusted under 35 U.S.C. 154(b) by 14 days.

(21) Appl. No.: 14/348,141

(22) PCT Filed: Sep. 28, 2012

(86) PCT No.: PCT/CA2012/050682
§ 371 (c)(1),
(2) Date: Mar. 28, 2014

(87) PCT Pub. No.: WO2013/044391
PCT Pub. Date: Apr. 4, 2013

(65) Prior Publication Data
US 2014/0235499 A1 Aug. 21, 2014

Related U.S. Application Data

(60) Provisional application No. 61/540,151, filed on Sep. 28, 2011.

(51) Int. Cl.
*G01N 33/00* (2006.01)
*G01N 33/50* (2006.01)

(52) U.S. Cl.
CPC ....... *G01N 33/5011* (2013.01); *G01N 33/5023* (2013.01); *G01N 2333/4703* (2013.01); *G01N 2500/10* (2013.01); *G01N 2800/7028* (2013.01)

(58) Field of Classification Search
CPC ... G01N 2500/00; G01N 25/10; G01N 25/20
USPC ............................................ 435/252.3, 320.1
See application file for complete search history.

(56) References Cited

U.S. PATENT DOCUMENTS

2004/0132108 A1* 7/2004 Hupp .................. C07K 14/4702
435/7.2

OTHER PUBLICATIONS

Servant et al. Differential regulation of p27(Kip1) expression by mitogenic and hypertrophie factors: Involvement of transcriptional and posttranscriptional mechanisms. The Journal of Cell Biology, vol. 148, No. 3, pp. 543-556, Feb. 7, 2000.
Shangary et al. Temporal activation of p53 by a specific MDM2 inhibitor is selectively toxic to tumors and leads to complete tumor growth inhibition. PNAS, Mar. 11, 2008, vol. 105, No. 10, pp. 3933-3938.
Shapiro—Cyclin-dependent kinase pathways as targets for cancer treatment. Journal of Clinical Oncology, vol. 24, No. 11, pp. 1770-1783, Apr. 10, 2006.
Sherr et al. Inhibitors of mammalian G1 cyclin-dependent kinases. Genes & Development, 9:1149-1163, 1995.
Sherr et al. CDK inhibitors: positive and negative regulators of G1-phase progression. Genes & Development, 1999 13:1501-1512.
Sterz et al. The potential of proteasome inhibitors in cancer therapy. Expert Opin Investig Drugs (2008) 17(6):879-895.
Strebhardt et al. Targeting polo-like kinase 1 for cancer therapy. Nature Reviews Cancer, vol. 6, pp. 321-330, Apr. 2006.
Takai et al. Polo-like kinases (Plks) and cancer. Oncogene (2005) 24, 287-291.
Topley et al. p21(WAF1/Cip1) functions as a suppressor of malignant skin tumor formation and a determinant of keratinocyte stem-cell potential. PNAS, vol. 96, pp. 9089-9094, Aug. 1999.
Ueki et al. Involvement of elevated expression of multiple cell-cycle regulator, DTURAMP (denticleless/RA-regulated nuclear matrix associated protein), in the growth of breast cancer cells. Oncogene (2008) 27, 5672-5683.
Van Nguyen et al. DNA damage-induced cellular senescence is sufficient to suppress tumorigenesis: a mouse model. J Exp Med, vol. 204, No. 6, pp. 1453-1461, Jun. 11, 2007.
Vassilev et al. In vivo activation of the p53 pathway by small-molecule antagonists of MDM2. Science 303, 844-848 (2004).
Ventura et al. Restoration of p53 function leads to tumour regression in vivo. Nature, vol. 445, pp. 661-665, Feb. 8, 2007.
Vogelstein et al. Surfing the p53 network. Nature, vol. 408, pp. 307-310, Nov. 16, 2000.
Wu et al. Cellular senescence is an important mechanism of tumor regression upon c-Myc inactivation. PNAS, vol. 104, No. 32, pp. 13028-13033, Aug. 7, 2007.
Yang et al. Small molecule inhibitors of HDM2 ubiquitin ligase activity stabilize and activate p53 in cells. Cancer Cell, Jun. 2005, vol. 7:547-559.
Yasui et al. TFDP1, CUL4A, and CDC16 identified as targets for amplification at 13q34 in hepatocellular carcinomas. Hepatology (2002) 35: 1476-1484.

(Continued)

*Primary Examiner* — Maryam Monshipouri
(74) *Attorney, Agent, or Firm* — Goudreau Gage Dubuc; Alain Dumont

(57) ABSTRACT

An assay and system compatible with high throughput screening (HTS) that is capable of identifying inhibitors, such as small-molecule inhibitors, of the degradation of the Cdk inhibitor p21, are described. The assay is based on the use of fusion protein comprising (i) a p2 polypeptide; and (i) a reporter protein linked to the C-terminal of said p21 polypeptide, wherein the fusion protein has a half-life that is similar to that of the p21 polypeptide. Inhibitors identified by this assay may be useful to inhibit the proliferation of tumor cells, and thus for the treatment of cancers.

20 Claims, 14 Drawing Sheets

(56) References Cited

OTHER PUBLICATIONS

Zhang et al. Bioluminescent imaging of Cdk2 inhibition in vivo. Nature Medecine, Jun. 2004, 10(6):643-648.
International Search Report and Written Opinion of corresponding International Application No. PCT/CA2012/050682, Dec. 2012.
Abbas et al. PCNA-dependent regulation of p21 ubiquitylation and degradation via the CRL4Cdt2 ubiquitin ligase complex. Genes & Development, 2008 22:2496-2506.
Abbas et al. p21 in cancer: intricate networks and multiple activities. Nature Rev Cancer Jun. 2009, vol. 9, pp. 400-414.
Abukhdeir et al. p21 and p27: roles in carcinogenesis and drug resistance. Expert Reviews in Molecular Medecine, vol. 10; e19; Jul. 2008.
Adams—The proteasome: a suitable antineoplastic target. Nature Reviews Cancer, vol. 4:349-360, May 2004.
Aghajan et al. Chemical genetics screen for enhancers of rapamycin identifies a specific inhibitor of an SCF family E3 ubiquitin ligase. Nature Biotechnology, vol. 28, No. 7, pp. 738-742, Jul. 2010.
Amador et al. APC/C(Cdc20) controls the ubiquitin-mediated degradation of p21 in prometaphase. Molecular Cell 27:462-473, Aug. 3, 2007.
Barboza et al.—p21 delays tumor onset by preservation of chromosomal stability, PNAS, Dec. 26, 2006, vol. 103, No. 52, pp. 19842-19847.
Bornstein et al. Role of the SCFSkp2 ubiquitin ligase in the degradation of p21 Cip1 in S phase. J Biol Chem 2003, 278:25752-25757.
Borriello et al. p57(Kip2) and cancer: time for a critical appraisal. Mol Cancer Res. 2011; 9:1269-84.
Cardozo et al. Wrenches in the works: drug discovery targeting the SCF ubiquitin ligase and APC/C complexes. BMC Biochemistry 2007, 8(Suppl I):S9.
Chang et al. Effects of p21Waf1/Cip1/Sdi1 on cellular gene expression: implications for carcinogenesis, senescence, and age-related diseases. PNAS, vol. 97, No. 8, pp. 4291-4296, Apr. 11, 2000.
Chen et al. The human homologue for the Caenorhabditis elegans cul-4 gene is amplified and overexpressed in primary breast cancers. Cancer Res 1998; 58:3677-3683.
Ciemerych et al. Cell cycle in mouse development. Oncogene (2005) 24, pp. 2877-2898.
Coats et al. Requirement of p27KiP1 for restriction point control of the fibroblasts cell cycle. Science 272:877880, May 10, 1996.
Coller et al. Expression analysis with oligonucleotide microarrays reveals that MYC regulates genes involved in growth, cell cycle, signaling, and adhesion. PNSA, vol. 97, No. 7, pp. 3260-3265, Mar. 28, 2000.
Deshaies et al. RING domain E3 ubiquitin ligases. Annu Rev Biochem 2009, 78:399-434.
El-Deiry et al. WAF1, a potential mediator of p53 tumor suppression. Cell vol. 75, pp. 817-825, Nov. 19, 1993.
Frescas et al. Deregulated proteolysis by the F-box proteins SKP2 and beta-TrCP: tipping the scales of cancer. Nature Rev Cancer, vol. 8, pp. 438-449, Jun. 2008.
Gartel et al. Lost in transcription: p21 repression, mechanisms, and consequences. Cancer Res 2005;65:3980-3985.
George et al. Loss of p21Waf1/Cip1/Sdi1 enhances intestinal stem cell survival following radiation injury. Am J Physiol Gastrointest Liver Physiol 296:G245-254, Dec. 4, 2008.
Hanahan et al. The hallmarks of cancer. Cell, vol. 100, 57-70, Jan. 7, 2000.
Hershko et al. The ubiquitin system. Annu Rev Biochem, 1998, 67:425-479.
Hoeller et al. Targetingthe ubiquitin system in cancer therapy. Nature vol. 458, pp. 438-444, Mar. 2009.
Jackson et al. Loss of the cell cycle inhibitors p21(Cip1) and p27(Kip1) enhances tumorigenesis in knockout mouse models. Oncogene (2002) 21, 8486-8497.
Keen et al. Aurora-kinase inhibitors as anticancer agents. Nature Reviews Cancer, vol. 4, Dec. 2004, pp. 927-936.
Kim et al. The CRL4Cdt2 ubiquitin ligase targets the degradation of p21 Cip1 to control replication licensing. Genes Dev. 2008 22:2507-2519.
Kitagawa et al. Ubiquitin-mediated control of oncogene and tumor suppressor gene products. Cancer Sci, Aug. 2009, vol. 100, No. 8, pp. 1374-1381.
Lapenna et al. Cell cycle kinases as therapeutic targets for cancer. Nature Reviews Drug Discovery, vol. 8, pp. 547-566, Jul. 2009.
Lee et al. Differential regulation of p53 and p21 by MKRN1 E3 ligase controls cell cycle arrest and apoptosis. The EMBO Journal, vol. 28, No. 14, pp. 2100-2113, 2009.
Lightcap et al. Proteasome inhibition measurements: clinical application. Clinical Chemistry 46:5, pp. 673-683 (2000).
Malumbres et al. Mammalian cyclin-dependent kinases. Trends in Biochemical Sciences, vol. 30, No. 11, Dec. 2005, pp. 630-641.
Malumbres et al. CDK inhibitors in cancer therapy: what is next? Trends Pharmacological Sciences, vol. 29, No. 1, pp. 16-21, 2008.
Malumbres et al. Cell cycle, CDKs and cancer: a changing paradigm. Nature Reviews Cancer, vol. 9, pp. 153-166, Mar. 2009.
Martin-Caballero et al. Tumor susceptibility of p21 (Waf1/Cip1)-deficient mice. Cancer Res, 2001; 61:6234-6238.
Marumoto et al. Aurora-A—a guardian of poles. Nature Reviews Cancer, vol. 5, pp. 42-50, Jan. 2005.
Moldovan et al. PCNA, the maestro of the replication fork. Cell 129, May 18, 2007, pp. 665-679.
Nakayama et al. Cip/Kip cyclin-dependent kinase inhibitors: brakes of the cell cycle engine during development. BioEssays 20: 1020-1029, 1998.
Nakayama et al. Ubiquitin ligases: cell-cycle control and cancer. Nature Reviews Cancer, vol. 6, pp. 369-381, May 2006.
Nalepa et al. Drug discovery in the ubiquitinproteasome system. Nature Reviews Drug Discovery, vol. 5, pp. 596-613, Jul. 2006.
Nickeleit et al. Argyrin a reveals a critical role for the tumor suppressor protein p27(kip1) in mediating antitumor activities in response to proteasome inhibition. Cancer Cell 14, 23-35, Jul. 2008.
Nishitani et al. CDK inhibitor p21 is degraded by a proliferating cell nuclear antigen-coupled Cu14-DDB1Cdt2 pathway during S phase and after UV irradiation. J Biol Chem, 2008, 283:29045-29052.
Nourse et al. Interleukin-2-mediated elimination of the p27KiP1 cyclin-dependent kinase inhibitor prevented by rapamycin. Nature, vol. 372, pp. 570-573, Dec. 8, 1994.
Orlicky et al. An allosteric inhibitor of substrate recognition by the SCF(Cdc4) ubiquitin ligase. Nature Biotechnology, vol. 28, No. 7, pp. 733-737, Jul. 2010.
Ortega et al. Cyclin D-dependent kinases, INK4 inhibitors and cancer. Biochimica Biophysica Acta 1602 (2002) 73-87.
Pan et al. Role of L2DTL, cell cycle-regulated nuclear and centrosome protein, in aggressive hepatocellular carcinoma. Cell Cycle, 2006, vol. 5, Issue 22, pp. 2676-2687.
Perez De Castro et al. Emerging cancer therapeutic opportunities by inhibiting mitotic kinases. Current Opinion Pharmacology 2008, 8:375-383.
Peterson et al. The p21Waf1 pathway is involved in blocking leukemogenesis by the t(8;21) fusion protein AML1-ETO. Blood 2007, 109:4392-4398.
Piva et al. CEP-18770: A novel, orally active proteasome inhibitor with a tumor-selective pharmacologic profile competitive with bortezomib. Blood 2008, 111:2765-2775.
Poole et al. Tumor suppressor functions for the Cdk inhibitor p21 in the mouse colon. Oncogene (2004) 23, 8128-8134.
Rico-Bautista et al. Chemical genetics approach to restoring p27Kip1 reveals novel compounds with antiproliferative activity in prostate cancer cells. BMC Biology, 2010, 8:153.

\* cited by examiner

A

B

```
   1 gttgtatatc agggccgcgc tgagctgcgc cagctgaggt gtgagcagct gccgaagtca
  61 gttccttgtg gagccggagc tgggcgcgga ttcgccgagg caccgaggca ctcagaggag
 121 gcgccatgtc agaaccggct ggggatgtcc gtcagaaccc atgcggcagc aaggcctgcc
 181 gccgcctctt cggcccagtg gacagcgagc agctgagccg cgactgtgat gcgctaatgg
 241 cgggctgcat ccaggaggcc cgtgagcgat ggaacttcga cttcgtcacc gagacaccac
 301 tggagggtga cttcgcctgg gagcgtgtgc ggggcctttgg cctgcccaag ctctaccttc
 361 ccacggggcc ccggcgaggc cgggatgagt tgggaggagg caggcggcct ggcacctcac
 421 ctgctctgct gcaggggaca gcagaggaag accatgtgga cctgtcactg tcttgtaccc
 481 ttgtgcctcg ctcaggggag caggctgaag ggtccccagg tggacctgga gactctcagg
 541 gtcgaaaacg gcggcagacc agcatgacag atttctacca ctccaaacgc cggctgatct
 601 tctccaagag gaagccctaa tccgcccaca ggaagcctgc agtcctggaa gcgcgagggc
 661 ctcaaaggcc cgctctacat cttctgcctt agtctcagtt tgtgtgtctt aattattatt
 721 tgtgttttaa tttaaacacc tcctcatgta catacccctgg ccgcccctg ccccccagcc
 781 tctggcatta gaattattta aacaaaaact aggcggttga atgagaggtt cctaagagtg
 841 ctgggcattt ttattttatg aaatactatt taaagcctcc tcatcccgtg ttctccttt
 901 cctctctccc ggaggttggg tgggccggct tcatgccagc tacttcctcc tccccacttg
 961 tccgctgggt ggtaccctct ggagggggtgt ggctccttcc catcgctgtc acaggcggtt
1021 atgaaattca ccccctttcc tggacactca gacctgaatt cttttttcatt tgagaagtaa
1081 acagatggca ctttgaaggg gcctcaccga gtggggcat catcaaaaac tttggagtcc
1141 cctcacctcc tctaaggttg ggcagggtga ccctgaagtg agcacagcct agggctgagc
1201 tggggacctg gtaccctcct ggctcttgat acccccctct gtcttgtgaa ggcagggga
1261 aggtggggtc ctggagcaga ccaccccgcc tgccctcatg gcccctctga cctgcactgg
1321 ggagcccgtc tcagtgttga gccttttccc tctttggctc cctgtacct tttgaggagc
1381 cccagctacc cttcttctcc agctgggctc tgcaattccc ctctgctgct gtccctcccc
1441 cttgtccttt cccttcagta ccctctcagc tccaggtggc tctgaggtgc ctgtcccacc
1501 cccacccccca gctcaatgga ctggaagggg aagggacaca caagaagaag ggcaccctag
1561 ttctacctca ggcagctcaa gcagcgaccg ccccctcctc tagctgtggg ggtgagggtc
1621 ccatgtggtg gcacaggccc ccttgagtgg ggttatctct gtgttagggg tatatgatgg
1681 gggagtagat cttctcagga gggagacact ggcccctcaa atcgtccagc gaccttcctc
1741 atccaccccca tccctcccca gttcattgca cttttgattag cagcggaaca aggagtcaga
1801 cattttaaga tggtggcagt agaggctatg gacagggcat gccacgtggg ctcatatggg
1861 gctgggagta gttgtctttc ctggcactaa cgttgagccc tggaggcac tgaagtgctt
1921 agtgtacttg gagtattggg gtctgacccc aaacaccttc cagctcctgt aacatactgg
1981 cctggactgt tttctctcgg ctccccatgt gtcctggttc ccgtttctcc acctagactg
2041 taaacctctc gagggcaggg accacaccct gtactgttct gtgtctttca cagctcctcc
2101 cacaatgctg aatatacagc aggtgctcaa taatgattc ttagtgactt tacttgtaaa
2161 aaaaaaaaaa aaaaa
```

FIG. 11A

```
  1 msepagdvrq npcgskacrr lfgpvdseql srdcdalmag ciqearerwn fdfvtetple
 61 gdfawervrg lglpklylpt gprrgrdelg ggrrpgtspa llqgtaeedh vdlslsctlv
121 prsgeqaegs pggpgdsqgr krrqtsmtdf yhskrrlifs krkp
```

FIG. 11B

```
   1 agcttaaaga tgacttcgaa agtttatgat ccagaacaaa ggaaacggat gataactggt
  61 ccgcagtggt gggccagatg taaacaaatg aatgttcttg attcatttat taattattat
 121 gattcagaaa aacatgcaga aaatgctgtt attttttac atggtaacgc ggcctcttct
 181 tatttatggc gacatgttgt gccacatatt gagccagtag cgcggtgtat tataccagat
 241 cttattggta tgggcaaatc aggcaaatct ggtaatggtt cttataggtt acttgatcat
 301 tacaaatatc ttactgcatg gtttgaactt cttaatttac caaagaagat cattttgtc
 361 ggccatgatt ggggtgcttg tttggcattt cattatagct atgagcatca agataagatc
 421 aaagcaatag ttcacgctga aagtgtagta gatgtgattg aatcatggga tgaatggcct
 481 gatattgaag aagatattgc gttgatcaaa tctgaagaag gagaaaaaat ggttttggag
 541 aataacttct tcgtggaaac catgttgcca tcaaaaatca tgagaaagtt agaaccagaa
 601 gaatttgcag catatcttga accattcaaa gagaaaggtg aagttcgtcg tccaacatta
 661 tcatggcctc gtgaaatccc gttagtaaaa ggtggtaaac ctgacgttgt acaaattgtt
 721 aggaattata atgcttatct acgtgcaagt gatgatttac caaaaatgtt tattgaatcg
 781 gatccaggat tcttttccaa tgctattgtt gaaggcgcca agaagtttcc taatactgaa
 841 tttgtcaaag taaaaggtct tcattttcg caagaagatg cacctgatga aatgggaaaa
 901 tatatcaaat cgttcgttga gcgagttctc aaaaatgaac aataattact ttggtttttt
 961 atttacattt ttcccggtt taataatata aatgtcattt tcaacaattt tattttaact
1021 gaatatttca cagggaacat tcatatatgt tgattaattt agctcgaact ttactctgtc
1081 atatcatttt ggaatattac ctctttcaat gaaactttat aaacagtggt tcaattaatt
1141 aatatatatt ataattacat ttgttatgta ataaactcgg ttttattata aaaaa
```

FIG. 12A

```
   1 mtskvydpeq rkrmitgpqw warckqmnvl dsfinyydse khaenavifl hgnaassylw
  61 rhvvphiepv arciipdlig mgksgksgng syrlldhyky ltawfellnl pkkiifvghd
 121 wgaclafhys yehqdkikai vhaesvvdvi eswdewpdie edialiksee gekmvlennf
 181 fvetmlpski mrklepeefa aylepfkekg evrrptlswp reiplvkggk pdvvqivrny
 241 naylrasddl pkmfiesdpg ffsnaivega kkfpntefvk vkglhfsqed apdemgkyik
 301 sfvervlkne q
```

FIG. 12B p21-Rluc protein fusion

DNA sequence

ATGTCAGAACCGGCTGGGGATGTCCGTCAGAACCCATGCGGCAGCAAGGCCTGC
CGCCGCCTCTTCGGCCCAGTGGACAGCGAGCAGCTGAGCCGCGACTGTGATGCGC
TAATGGCGGGCTGCATCCAGGAGGCCCGTGAGCGATGGAACTTCGACTTTGTCAC
CGAGACACCACTGGAGGGTGACTTCGCCTGGGAGCGTGTGCGGGGCCTTGGCCTG
CCCAAGCTCTACCTTCCCACGGGGCCCCGGCGAGGCCGGGATGAGTTGGGAGGA
GGCAGGCGGCCTGGCACCTCACCTGCTCTGCTGCAGGGGACAGCAGAGGAAGAC
CATGTGGACCTGTCACTGTCTTGTACCCTTGTGCCTCGCTCAGGGGAGCAGGCTG
AAGGGTCCCCAGGTGGACCTGGAGACTCTCAGGGTCGAAAACGGCGGCAGACCA
GCATGACAGATTTCTACCACTCCAAACGCCGGCTGATCTTCTCCAAGAGGAAGCC
CGGTACCATGACCAGCAAGGTGTACGACCCCGAGCAGAGGAAGAGGATGATCAC
CGGCCCCCAGTGGTGGGCCAGGTGCAAGCAGATGAACGTGCTGGACAGCTTCAT
CAACTACTACGACAGCGAGAAGCACGCCGAGAACGCCGTGATCTTCCTGCACGG
CAACGCCGCTAGCAGCTACCTGTGGAGGCACGTGGTGCCCCACATCGAGCCCGTG
GCCAGGTGCATCATCCCCGATCTGATCGGCATGGGCAAGAGCGGCAAGAGCGGC
AACGGCAGCTACAGGCTGCTGGACCACTACAAGTACCTGACCGCCTGGTTCGAGC
TCCTGAACCTGCCCAAGAAGATCATCTTCGTGGGCCACGACTGGGGCGCCTGCCT
GGCCTTCCACTACAGCTACGAGCACCAGGACAAGATCAAGGCCATCGTGCACGC
CGAGAGCGTGGTGGACGTGATCGAGAGCTGGGACGAGTGGCCAGACATCGAGGA
GGACATCGCCCTGATCAAGAGCGAGGAGGGCGAGAAGATGGTGCTGGAGAACAA
CTTCTTCGTGGAGACCATGCTGCCCAGCAAGATCATGAGAAAGCTGGAGCCCGAG
GAGTTCGCCGCCTACCTGGAGCCCTTCAAGGAGAAGGGCGAGGTGAGAAGACCC
ACCCTGAGCTGGCCCAGAGAGATCCCCCTGGTGAAGGGCGGCAAGCCCGACGTG
GTGCAGATCGTGAGAAACTACAACGCCTACCTGAGAGCCAGCGACGACCTGCCC
AAGATGTTCATCGAGAGCGACCCCGGCTTCTTCAGCAACGCCATCGTGGAGGGCG
CCAAGAAGTTCCCCAACACCGAGTTCGTGAAGGTGAAGGGCCTGCACTTCAGCCA
GGAGGACGCCCCCGACGAGATGGGCAAGTACATCAAGAGCTTCGTGGAGAGAGT
GCTGAAGAACGAGCAGTAA

*ATG start codon and TAA stop codon are underlined
GGTACC = linker between p21 and Renilla luciferase (KpnI restriction site)

Protein

MSEPAGDVRQNPCGSKACRRLFGPVDSEQLSRDCDALMAGCIQEARERWNFDFVTE
TPLEGDFAWERVRGLGLPKLYLPTGPRRGRDELGGGRRPGTSPALLQGTAEEDHVDL
SLSCTLVPRSGEQAEGSPGGPGDSQGRKRRQTSMTDFYHSKRRLIFSKRKPGT*MTSKV*
*YDPEQRKRMITGPQWWARCKQMNVLDSFINYYDSEKHAENAVIFLHGNAASSYLWRHVVP*
*HIEPVARCIIPDLIGMGKSGKSGNGSYRLLDHYKYLTAWFELLNLPKKIIFVGHDWGACLA*
*FHYSYEHQDKIKAIVHAESVVDVIESWDEWPDIEEDIALIKSEEGEKMVLENNFFVETMLPS*
*KIMRKLEPEEFAAYLEPFKEKGEVRRPTLSWPREIPLVKGGKPDVVQIVRNYNAYLRASDD*
*LPKMFIESDPGFFSNAIVEGAKKFPNTEFVKVKGLHFSQEDAPDEMGKYIKSFVERVLKNE*
*Q*

FIG. 13

```
   1 cttcttcgtc agcctccctt ccaccgccat attgggccac taaaaaaagg gggctcgtct
  61 tttcggggtg ttttttctccc cctccctgt cccgcttgc tcacggctct gcgactccga
 121 cgccggcaag gtttggagag cggctgggtt cgcgggaccc gcgggcttgc acccgcccag
 181 actcggacgg gctttgccac cctctccgct tgcctggtcc cctctcctct ccgccctccc
 241 gctcgccagt ccatttgatc agcggagact cggcggccgg gccggggctt ccccgcagcc
 301 cctgcgcgct cctagagctc gggccgtggc tcgtcggggt ctgtgtcttt tggctccgag
 361 ggcagtcgct gggcttccga gaggggttcg ggctgcgtag gggcgctttg ttttgttcgg
 421 ttttgttttt ttgagagtgc gagagaggcg gtcgtgcaga cccgggagaa agatgtcaaa
 481 cgtgcgagtg tctaacggga gccctagcct ggagcggatg gacgccaggc aggcggagca
 541 ccccaagccc tcggcctgca ggaacctctt cggcccggtg gaccacgaag agttaacccg
 601 ggacttggag aagcactgca gagacatgga agaggcgagc cagcgcaagt ggaatttcga
 661 ttttcagaat cacaaacccc tagagggcaa gtacgagtgg caagaggtgg agaagggcag
 721 cttgcccgag ttctactaca gacccccgcg gcccccaaa ggtgcctgca aggtgccggc
 781 gcaggagagc caggatgtca gcgggagccg cccggcggcg cctttaattg gggctccggc
 841 taactctgag gacacgcatt tggtggaccc aaagactgat ccgtcggaca gccagacggg
 901 gttagcggag caatgcgcag gaataaggaa gcgacctgca accgacgatt cttctactca
 961 aaacaaaaga gccaacagaa cagaagaaaa tgtttcagac ggttccccaa atgccggttc
1021 tgtggagcag acgccagaga gcctggcct cagaagacgt caaacgtaaa cagctcgaat
1081 taagaatatg tttccttgtt tatcagatac atcactgctt gatgaagcaa ggaagatata
1141 catgaaaatt ttaaaaatac atatcgctga cttcatggaa tggacatcct gtataagcac
1201 tgaaaaacaa caacacaata acactaaaat tttaggcact cttaaatgat ctgcctctaa
1261 aagcgttgga tgtagcatta tgcaattagg ttttttcctta tttgcttcat tgtactacct
1321 gtgtatatag tttttacctt ttatgtagca cataaacttt ggggaaggga gggcagggtg
1381 gggctgagga actgacgtgg agcgggtat gaagagcttg ctttgattta cagcaagtag
1441 ataaatattt gacttgcatg aagagaagca attttgggga agggtttgaa ttgttttctt
1501 taaagatgta atgtcccttt cagagacagc tgatacttca tttaaaaaaa tcacaaaaat
1561 ttgaacactg gctaaagata attgctattt attttacaa gaagtttatt ctcatttggg
1621 agatctggtg atctcccaag ctatctaaag tttgttagat agctgcatgt ggctttttta
1681 aaaaagcaac agaaacctat cctcactgcc ctcccagtc tctcttaaag ttggaattta
1741 ccagttaatt actcagcaga atggtgatca ctccaggtag tttggggcaa aaatccgagg
1801 tgcttgggag ttttgaatgt taagaattga ccatctgctt ttattaaatt tgttgacaaa
1861 attttctcat tttcttttca cttcgggctg tgtaaacaca gtcaaaataa ttctaaatcc
1921 ctcgatattt ttaaagatct gtaagtaact tcacattaaa aaatgaaata tttttttaatt
1981 taaagcttac tctgtccatt tatccacagg aaagtgttat ttttcaagga aggttcatgt
2041 agagaaaagc acacttgtag gataagtgaa atggatacta catctttaaa cagtatttca
2101 ttgcctgtgt atggaaaaac catttgaagt gtacctgtgt acataactct gtaaaaacac
2161 tgaaaaatta tactaactta tttatgttaa aagatttttt ttaatctaga caatatacaa
2221 gccaaagtgg catgttttgt gcatttgtaa atgctgtgtt gggtagaata ggttttcccc
2281 tcttttgtta aataatatgg ctatgcttaa aaggttgcat actgagccaa gtataatttt
2341 ttgtaatgtg tgaaaaagat gccaattatt gttacacatt aagtaatcaa taaagaaaac
2401 ttccatagct att
```

FIG. 14A

```
   1 msnvrvsngs pslermdarq aehpkpsacr nlfgpvdhee ltrdlekhcr dmeeasqrkw
  61 nfdfqnhkpl egkyewqeve kgslpefyyr pprppkgack vpaqesqdvs gsrpaaplig
 121 apansedthl vdpktdpsds qtglaeqcag irkrpatdds stqnkranrt eenvsdgspn
 181 agsveqtpkk pglrrrqt
```

FIG. 14B

```
   1 agtgcgctgt gctcgagggg tgccggccag gcctgagcga gcgagctagc cagcaggcat
  61 cgagggggcg cggctgccgt ccggacgaga caggcgaacc cgacgcagaa gagtccacca
 121 ccggacagcc aggtagccgc cgcgtccctc gcacacgcag agtcgggcgg cgcggggtct
 181 cccttgcgcc cggcctccgc cctctcctcc tctcctttcc ccttcttctc gctgtcctct
 241 cctctctcgc tgcccgcgtt tgcgcagccc cgggccatgt ccgacgcgtc cctccgcagc
 301 acatccacga tggagcgtct tgtcgcccgt gggaccttcc cagtactagt gcgcaccagc
 361 gcctgccgca gcctcttcgg gccggtggac cacgaggagc tgagccgcga gctgcaggcc
 421 cgcctggccg agctgaacgc cgaggaccag aaccgctggg attacgactt ccagcaggac
 481 atgccgctgc ggggccctgg acgcctgcag tggaccgaag tggacagcga ctcggtgccc
 541 gcgttctacc gcgagacggt gcaggtgggg cgctgccgcc tgctgctggc gccgcgcccc
 601 gtcgcggtcg cggtggctgt cagcccgccc ctcgagccgg ccgctgagtc cctcgacggc
 661 ctcgaggagg cgccggagca gctgcctagt gtcccggtcc cggccccggc gtccaccccg
 721 cccccagtcc cggtcctggc tccagccccg gccccggctc cggctccggt cgcggctccg
 781 gtcgcggctc cggtcgcggt cgcggtcctg gccccggccc cggccccggc tccggctccg
 841 gctccggccc cggctccagt cgcggccccg gccccagccc cggccccggc cccggccccg
 901 gccccccggc cggccccggc cccggacgcg gcgcctcaag agagcgcgag gcagggcgcg
 961 aaccagggc agcgcggcca ggagcctctc gctgaccagc tgcactcggg gatttcggga
1021 cgtcccgcgg ccggcaccgc ggccgccagc gccaacggcg cggcgatcaa gaagctgtcc
1081 gggcctctga tctccgattt cttcgccaag cgcaagagat cagcgcctga gaagtcgtcg
1141 ggcgatgtcc ccgcgccgtg tccctctcca agcgccgccc ctggcgtggg ctcggtggag
1201 cagacccccg gcaagaggct gcggtgagcc aatttagagc ccaaagagcc ccgagggaac
1261 ctgccgggc agcggacgtt ggaagggcgc tgggcctcgg ctgggaccgt tcatgtagca
1321 gcaaccggcg gcggctgccg cagagcagcg ttcggttttg ttttaaatt ttgaaaactg
1381 tgcaatgtat taataacgtc ttttatatc taaatgtatt ctgcacgaga aggtacactg
1441 gtcccaaggt gtaaagcttt aagagtcatt tatataaat gtttaatctc tgctgaaact
1501 cagtgcaaaa aaaagaaaaa agaaaaaaaa aaggaaaaaa taaaaaaacc atgtatattt
1561 gtacaaaaag tttttaaagt tatactaact tatatttct atttatgtcc aggcgtggac
1621 cgctctgcca cgcactagct cggttattgg ttatgccaaa ggcactctcc atctcccaca
1681 tctggttatt gacaagtgta actttatttt catcgcggac tctggggaag ggggtcactc
1741 acaagctgta gctgccatac atgcccatct agcttgcagt ctcttcgcgc tttcgctgtc
1801 tctcttatta tgactgtgtt tatctgaaac ttgaagacaa gtctgttaaa atggttcctg
1861 agccgtctgt accactgccc cggcccctcg tccgccgggt tctaaataaa gaggccgaaa
1921 aatgctgcaa aaaaaaaaa aaa
```

FIG. 15A

```
   1 msdaslrsts tmerlvargt fpvlvrtsac rslfgpvdhe elsrelqarl aelnaedqnr
  61 wdydfqqdmp lrgpgrlqwt evdsdsvpaf yretvqvgrc rlllaprpva vavavspple
 121 paaesldgle eapeqlpsvp vpapastppp vpvlapapap apapvaapva apvavavlap
 181 apapapapap apapvaapap apapapapap apapapdaap qesaeqganq gqrgqeplad
 241 qlhsgisgrp aagtaaasan gaaikklsgp lisdffakrk rsapekssgd vpapcpspsa
 301 apgvgsveqt prkrlr
```

FIG. 15B

SEQUENCE LISTING

```
<160> NUMBER OF SEQ ID NOS: 10

<210> SEQ ID NO 1
<211> LENGTH: 2175
<212> TYPE: DNA
<213> ORGANISM: Homo sapiens
<220> FEATURE:
<221> NAME/KEY: CDS
<222> LOCATION: (126)..(620)

<400> SEQUENCE: 1
gttgtatatc agggccgcgc tgagctgcgc cagctgaggt gtgagcagct gccgaagtca      60
gttccttgtg gagccggagc tgggcgcgga ttcgccgagg cacccgaggca ctcagaggag     120 gcgcc atg tca gaa ccg gct ggg gat gtc cgt cag aac cca tgc ggc agc     170
      Met Ser Glu Pro Ala Gly Asp Val Arg Gln Asn Pro Cys Gly Ser
      1               5                  10                  15 aag gcc tgc cgc cgc ctc ttc ggc cca gtg gac agc gag cag ctg agc     218
Lys Ala Cys Arg Arg Leu Phe Gly Pro Val Asp Ser Glu Gln Leu Ser
             20                  25                  30 cgc gac tgt gat gcg cta atg gcg ggc tgc atc cag gag gcc cgt gag     266
Arg Asp Cys Asp Ala Leu Met Ala Gly Cys Ile Gln Glu Ala Arg Glu
         35                  40                  45 cga tgg aac ttc gac ttt gtc acc gag aca cca ctg gag ggt gac ttc     314
Arg Trp Asn Phe Asp Phe Val Thr Glu Thr Pro Leu Glu Gly Asp Phe
     50                  55                  60 gcc tgg gag cgt gtg cgg ggc ctt ggc ctg ccc aag ctc tac ctt ccc     362
Ala Trp Glu Arg Val Arg Gly Leu Gly Leu Pro Lys Leu Tyr Leu Pro
 65                  70                  75 acg ggg ccc cgg cga ggc cgg gat gag ttg gga gga ggc agg cgg cct     410
Thr Gly Pro Arg Arg Gly Arg Asp Glu Leu Gly Gly Gly Arg Arg Pro
 80                  85                  90                  95 ggc acc tca cct gct ctg ctg cag ggg aca gca gag gaa gac cat gtg     458
```

```
Gly Thr Ser Pro Ala Leu Leu Gln Gly Thr Ala Glu Glu Asp His Val
                100                 105                 110 gac ctg tca ctg tct tgt acc ctt gtg cct cgc tca ggg gag cag gct        506
Asp Leu Ser Leu Ser Cys Thr Leu Val Pro Arg Ser Gly Glu Gln Ala
            115                 120                 125 gaa ggg tcc cca ggt gga cct gga gac tct cag ggt cga aaa cgg cgg        554
Glu Gly Ser Pro Gly Gly Pro Gly Asp Ser Gln Gly Arg Lys Arg Arg
        130                 135                 140 cag acc agc atg aca gat ttc tac cac tcc aaa cgc cgg ctg atc ttc        602
Gln Thr Ser Met Thr Asp Phe Tyr His Ser Lys Arg Arg Leu Ile Phe
    145                 150                 155 tcc aag agg aag ccc taa tccgcccaca ggaagcctgc agtcctggaa               650
Ser Lys Arg Lys Pro
160 gcgcgagggc tcaaaggcc cgctctacat cttctgcctt agtctcagtt tgtgtgtctt       710 aattattatt tgtgttttaa tttaaacacc tcctcatgta catacccctgg ccgcccctg      770 cccccagcc tctggcatta gaattattta acaaaaact aggcggttga atgagaggtt        830 cctaagagtg ctgggcattt ttattttatg aaatactatt taaagcctcc tcatcccgtg     890 ttctcctttt cctctctccc ggaggttggg tgggccggct tcatgccagc tacttcctcc     950 tccccacttg tccgctgggt ggtaccctct ggaggggtgt ggctccttcc catcgctgtc    1010 acaggcggtt atgaaattca cccccttttcc tggacactca gacctgaatt ctttttcatt   1070 tgagaagtaa acagatggca cttttgaaggg gcctcaccga gtgggggcat catcaaaaac   1130 tttggagtcc cctcacctcc tctaaggttg gcagggtga ccctgaagtg agcacagcct     1190 agggctgagc tggggacctg gtaccctcct ggctcttgat accccctct gtcttgtgaa     1250 ggcaggggga aggtgggggtc ctggagcaga ccaccccgcc tgccctcatg gcccctctga   1310 cctgcactgg ggagcccgtc tcagtgttga gccttttccc tctttggctc ccctgtacct   1370 tttgaggagc cccagctacc cttcttctcc agctgggctc tgcaattccc ctctgctgct   1430 gtccctcccc cttgtccttt cccttcagta ccctctcagc tccaggtggc tctgaggtgc   1490 ctgtcccacc cccaccccca gctcaatgga ctggaagggg aagggacaca caagaagaag   1550 ggcaccctag ttctacctca ggcagctcaa gcagcgaccg ccccctcctc tagctgtggg   1610 ggtgagggtc ccatgtggtg gcacaggcc ccttgagtgg ggttatctct gtgttagggg     1670 tatatgatgg gggagtagat cttttctagga gggagacact ggcccctcaa atcgtccagc   1730 gaccttcctc atccacccca tccctcccca gttcattgca ctttgattag cagcggaaca   1790 aggagtcaga cattttaaga tggtggcagt agaggctatg gcagggcat gccacgtggg    1850 ctcatatggg gctgggagta gttgtctttc ctggcactaa cgttgagccc ctggaggcac   1910 tgaagtgctt agtgtacttg gagtattggg gtctgacccc aaacaccttc cagctcctgt   1970 aacatactgg cctggactgt tttctctcgg ctccccatgt gtcctggttc ccgtttctcc   2030 acctagactg taaacctctc gagggcaggg accacaccct gtactgttct gtgtctttca   2090 cagctcctcc cacaatgctg aatatacagc aggtgctcaa taaatgattc ttagtgactt   2150 tacttgtaaa aaaaaaaaa aaaaa                                           2175

<210> SEQ ID NO 2
<211> LENGTH: 164
<212> TYPE: PRT
<213> ORGANISM: Homo sapiens

<400> SEQUENCE: 2
```

```
Met Ser Glu Pro Ala Gly Asp Val Arg Gln Asn Pro Cys Gly Ser Lys
1               5                   10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
        35                  40                      45

Trp Asn Phe Asp Phe Val Thr Glu Thr Pro Leu Glu Gly Asp Phe Ala
    50                  55                  60

Trp Glu Arg Val Arg Gly Leu Gly Leu Pro Lys Leu Tyr Leu Pro Thr
65                  70                  75                  80

Gly Pro Arg Arg Gly Arg Asp Glu Leu Gly Gly Arg Arg Pro Gly
                85                  90                  95

Thr Ser Pro Ala Leu Leu Gln Gly Thr Ala Glu Glu Asp His Val Asp
                100                 105                 110

Leu Ser Leu Ser Cys Thr Leu Val Pro Arg Ser Gly Glu Gln Ala Glu
                115                 120                 125

Gly Ser Pro Gly Gly Pro Gly Asp Ser Gln Gly Arg Lys Arg Arg Gln
    130                 135                 140

Thr Ser Met Thr Asp Phe Tyr His Ser Lys Arg Arg Leu Ile Phe Ser
145                 150                 155                 160

Lys Arg Lys Pro

<210> SEQ ID NO 3
<211> LENGTH: 1211
<212> TYPE: DNA
<213> ORGANISM: Renilla reniformis
<220> FEATURE:
<221> NAME/KEY: CDS
<222> LOCATION: (10)..(945)

<400> SEQUENCE: 3 agcttaaag atg act tcg aaa gtt tat gat cca gaa caa agg aaa cgg atg      51
          Met Thr Ser Lys Val Tyr Asp Pro Glu Gln Arg Lys Arg Met
          1               5                   10 ata act ggt ccg cag tgg tgg gcc aga tgt aaa caa atg aat gtt ctt        99
Ile Thr Gly Pro Gln Trp Trp Ala Arg Cys Lys Gln Met Asn Val Leu
15                  20                  25                  30 gat tca ttt att aat tat tat gat tca gaa aaa cat gca gaa aat gct      147
Asp Ser Phe Ile Asn Tyr Tyr Asp Ser Glu Lys His Ala Glu Asn Ala
                35                  40                  45 gtt att ttt tta cat ggt aac gcg gcc tct tct tat tta tgg cga cat      195
Val Ile Phe Leu His Gly Asn Ala Ala Ser Ser Tyr Leu Trp Arg His
            50                  55                  60 gtt gtg cca cat att gag cca gta gcg cgg tgt att ata cca gat ctt      243
Val Val Pro His Ile Glu Pro Val Ala Arg Cys Ile Ile Pro Asp Leu
        65                  70                  75 att ggt atg ggc aaa tca ggc aaa tct ggt aat ggt tct tat agg tta      291
Ile Gly Met Gly Lys Ser Gly Lys Ser Gly Asn Gly Ser Tyr Arg Leu
80                  85                  90 ctt gat cat tac aaa tat ctt act gca tgg ttt gaa ctt ctt aat tta      339
Leu Asp His Tyr Lys Tyr Leu Thr Ala Trp Phe Glu Leu Leu Asn Leu
95                  100                 105                 110 cca aag aag atc att ttt gtc ggc cat gat tgg ggt gct tgt ttg gca      387
Pro Lys Lys Ile Ile Phe Val Gly His Asp Trp Gly Ala Cys Leu Ala
                115                 120                 125 ttt cat tat agc tat gag cat caa gat aag atc aaa gca ata gtt cac      435
Phe His Tyr Ser Tyr Glu His Gln Asp Lys Ile Lys Ala Ile Val His
            130                 135                 140
```

```
gct gaa agt gta gta gat gtg att gaa tca tgg gat gaa tgg cct gat      483
Ala Glu Ser Val Val Asp Val Ile Glu Ser Trp Asp Glu Trp Pro Asp
        145                 150                 155 att gaa gaa gat att gcg ttg atc aaa tct gaa gaa gga gaa aaa atg      531
Ile Glu Glu Asp Ile Ala Leu Ile Lys Ser Glu Glu Gly Glu Lys Met
    160                 165                 170 gtt ttg gag aat aac ttc ttc gtg gaa acc atg ttg cca tca aaa atc      579
Val Leu Glu Asn Asn Phe Phe Val Glu Thr Met Leu Pro Ser Lys Ile
175                 180                 185                 190 atg aga aag tta gaa cca gaa gaa ttt gca gca tat ctt gaa cca ttc      627
Met Arg Lys Leu Glu Pro Glu Glu Phe Ala Ala Tyr Leu Glu Pro Phe
            195                 200                 205 aaa gag aaa ggt gaa gtt cgt cgt cca aca tta tca tgg cct cgt gaa      675
Lys Glu Lys Gly Glu Val Arg Arg Pro Thr Leu Ser Trp Pro Arg Glu
        210                 215                 220 atc ccg tta gta aaa ggt ggt aaa cct gac gtt gta caa att gtt agg      723
Ile Pro Leu Val Lys Gly Gly Lys Pro Asp Val Val Gln Ile Val Arg
    225                 230                 235 aat tat aat gct tat cta cgt gca agt gat gat tta cca aaa atg ttt      771
Asn Tyr Asn Ala Tyr Leu Arg Ala Ser Asp Asp Leu Pro Lys Met Phe
240                 245                 250 att gaa tcg gat cca gga ttc ttt tcc aat gct att gtt gaa ggc gcc      819
Ile Glu Ser Asp Pro Gly Phe Phe Ser Asn Ala Ile Val Glu Gly Ala
255                 260                 265                 270 aag aag ttt cct aat act gaa ttt gtc aaa gta aaa ggt ctt cat ttt      867
Lys Lys Phe Pro Asn Thr Glu Phe Val Lys Val Lys Gly Leu His Phe
            275                 280                 285 tcg caa gaa gat gca cct gat gaa atg gga aaa tat atc aaa tcg ttc      915
Ser Gln Glu Asp Ala Pro Asp Glu Met Gly Lys Tyr Ile Lys Ser Phe
        290                 295                 300 gtt gag cga gtt ctc aaa aat gaa caa taa ttactttggt tttttattta       965
Val Glu Arg Val Leu Lys Asn Glu Gln
            305                 310 cattttccc gggtttaata atataaatgt cattttcaac aatttatttt taactgaata   1025
tttcacaggg aacattcata tatgttgatt aatttagctc gaactttact ctgtcatatc  1085
attttggaat attacctctt tcaatgaaac tttataaaca gtggttcaat taattaatat  1145
atattataat tacatttgtt atgtaataaa ctcggtttta ttataaaaaa aaaaaaaaaa  1205
aaaaaa                                                             1211

<210> SEQ ID NO 4
<211> LENGTH: 311
<212> TYPE: PRT
<213> ORGANISM: Renilla reniformis

<400> SEQUENCE: 4

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
            85                  90                  95
```

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
            115                 120                 125

Tyr Ser Tyr Glu His Gln Asp Lys Ile Lys Ala Ile Val His Ala Glu
130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
            195                 200                 205

Lys Gly Glu Val Arg Arg Pro Thr Leu Ser Trp Pro Arg Glu Ile Pro
            210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
            275                 280                 285

Glu Asp Ala Pro Asp Glu Met Gly Lys Tyr Ile Lys Ser Phe Val Glu
            290                 295                 300

Arg Val Leu Lys Asn Glu Gln
305                 310

<210> SEQ ID NO 5
<211> LENGTH: 1434
<212> TYPE: DNA
<213> ORGANISM: Artificial Sequence
<220> FEATURE:
<223> OTHER INFORMATION: Synthetic fusion construct
<220> FEATURE:
<221> NAME/KEY: CDS
<222> LOCATION: (1)..(1434)

<400> SEQUENCE: 5

```
atg tca gaa ccg gct ggg gat gtc cgt cag aac cca tgc ggc agc aag      48
Met Ser Glu Pro Ala Gly Asp Val Arg Gln Asn Pro Cys Gly Ser Lys
1               5                   10                  15 gcc tgc cgc cgc ctc ttc ggc cca gtg gac agc gag cag ctg agc cgc      96
Ala Cys Arg Arg Leu Phe Gly Pro Val Asp Ser Glu Gln Leu Ser Arg
                20                  25                  30 gac tgt gat gcg cta atg gcg ggc tgc atc cag gag gcc cgt gag cga     144
Asp Cys Asp Ala Leu Met Ala Gly Cys Ile Gln Glu Ala Arg Glu Arg
            35                  40                  45 tgg aac ttc gac ttt gtc acc gag aca cca ctg gag ggt gac ttc gcc     192
Trp Asn Phe Asp Phe Val Thr Glu Thr Pro Leu Glu Gly Asp Phe Ala
        50                  55                  60 tgg gag cgt gtg cgg ggc ctt ggc ctg ccc aag ctc tac ctt ccc acg     240
Trp Glu Arg Val Arg Gly Leu Gly Leu Pro Lys Leu Tyr Leu Pro Thr
65                  70                  75                  80 ggg ccc cgg cga ggc cgg gat gag ttg gga gga ggc agg cgg cct ggc     288
Gly Pro Arg Arg Gly Arg Asp Glu Leu Gly Gly Gly Arg Arg Pro Gly
                85                  90                  95
```

-continued

```
acc tca cct gct ctg ctg cag ggg aca gca gag gaa gac cat gtg gac    336
Thr Ser Pro Ala Leu Leu Gln Gly Thr Ala Glu Glu Asp His Val Asp
            100                 105                 110 ctg tca ctg tct tgt acc ctt gtg cct cgc tca ggg gag cag gct gaa    384
Leu Ser Leu Ser Cys Thr Leu Val Pro Arg Ser Gly Glu Gln Ala Glu
        115                 120                 125 ggg tcc cca ggt gga cct gga gac tct cag ggt cga aaa cgg cgg cag    432
Gly Ser Pro Gly Gly Pro Gly Asp Ser Gln Gly Arg Lys Arg Arg Gln
130                 135                 140 acc agc atg aca gat ttc tac cac tcc aaa cgc cgg ctg atc ttc tcc    480
Thr Ser Met Thr Asp Phe Tyr His Ser Lys Arg Arg Leu Ile Phe Ser
145                 150                 155                 160 aag agg aag ccc ggt acc atg acc agc aag gtg tac gac ccc gag cag    528
Lys Arg Lys Pro Gly Thr Met Thr Ser Lys Val Tyr Asp Pro Glu Gln
                165                 170                 175 agg aag agg atg atc acc ggc ccc cag tgg tgg gcc agg tgc aag cag    576
Arg Lys Arg Met Ile Thr Gly Pro Gln Trp Trp Ala Arg Cys Lys Gln
            180                 185                 190 atg aac gtg ctg gac agc ttc atc aac tac tac gac agc gag aag cac    624
Met Asn Val Leu Asp Ser Phe Ile Asn Tyr Tyr Asp Ser Glu Lys His
        195                 200                 205 gcc gag aac gcc gtg atc ttc ctg cac ggc aac gcc gct agc agc tac    672
Ala Glu Asn Ala Val Ile Phe Leu His Gly Asn Ala Ala Ser Ser Tyr
210                 215                 220 ctg tgg agg cac gtg gtg ccc cac atc gag ccc gtg gcc agg tgc atc    720
Leu Trp Arg His Val Val Pro His Ile Glu Pro Val Ala Arg Cys Ile
225                 230                 235                 240 atc ccc gat ctg atc ggc atg ggc aag agc ggc aag agc ggc aac ggc    768
Ile Pro Asp Leu Ile Gly Met Gly Lys Ser Gly Lys Ser Gly Asn Gly
                245                 250                 255 agc tac agg ctg ctg gac cac tac aag tac ctg acc gcc tgg ttc gag    816
Ser Tyr Arg Leu Leu Asp His Tyr Lys Tyr Leu Thr Ala Trp Phe Glu
            260                 265                 270 ctc ctg aac ctg ccc aag aag atc atc ttc gtg ggc cac gac tgg ggc    864
Leu Leu Asn Leu Pro Lys Lys Ile Ile Phe Val Gly His Asp Trp Gly
        275                 280                 285 gcc tgc ctg gcc ttc cac tac agc tac gag cac cag gac aag atc aag    912
Ala Cys Leu Ala Phe His Tyr Ser Tyr Glu His Gln Asp Lys Ile Lys
290                 295                 300 gcc atc gtg cac gcc gag agc gtg gtg gac gtg atc gag agc tgg gac    960
Ala Ile Val His Ala Glu Ser Val Val Asp Val Ile Glu Ser Trp Asp
305                 310                 315                 320 gag tgg cca gac atc gag gag gac atc gcc ctg atc aag agc gag gag    1008
Glu Trp Pro Asp Ile Glu Glu Asp Ile Ala Leu Ile Lys Ser Glu Glu
                325                 330                 335 ggc gag aag atg gtg ctg gag aac aac ttc ttc gtg gag acc atg ctg    1056
Gly Glu Lys Met Val Leu Glu Asn Asn Phe Phe Val Glu Thr Met Leu
            340                 345                 350 ccc agc aag atc atg aga aag ctg gag ccc gag gag ttc gcc gcc tac    1104
Pro Ser Lys Ile Met Arg Lys Leu Glu Pro Glu Glu Phe Ala Ala Tyr
        355                 360                 365 ctg gag ccc ttc aag gag aag ggc gag gtg aga aga ccc acc ctg agc    1152
Leu Glu Pro Phe Lys Glu Lys Gly Glu Val Arg Arg Pro Thr Leu Ser
370                 375                 380 tgg ccc aga gag atc ccc ctg gtg aag ggc ggc aag ccc gac gtg gtg    1200
Trp Pro Arg Glu Ile Pro Leu Val Lys Gly Gly Lys Pro Asp Val Val
385                 390                 395                 400 cag atc gtg aga aac tac aac gcc tac ctg aga gcc agc gac gac ctg    1248
Gln Ile Val Arg Asn Tyr Asn Ala Tyr Leu Arg Ala Ser Asp Asp Leu
```

```
                    405                 410                 415
ccc aag atg ttc atc gag agc gac ccc ggc ttc ttc agc aac gcc atc       1296
Pro Lys Met Phe Ile Glu Ser Asp Pro Gly Phe Phe Ser Asn Ala Ile
        420                 425                 430 gtg gag ggc gcc aag aag ttc ccc aac acc gag ttc gtg aag gtg aag       1344
Val Glu Gly Ala Lys Lys Phe Pro Asn Thr Glu Phe Val Lys Val Lys
            435                 440                 445 ggc ctg cac ttc agc cag gag gac gcc ccc gac gag atg ggc aag tac       1392
Gly Leu His Phe Ser Gln Glu Asp Ala Pro Asp Glu Met Gly Lys Tyr
    450                 455                 460 atc aag agc ttc gtg gag aga gtg ctg aag aac gag cag taa               1434
Ile Lys Ser Phe Val Glu Arg Val Leu Lys Asn Glu Gln
465                 470                 475

<210> SEQ ID NO 6
<211> LENGTH: 477
<212> TYPE: PRT
<213> ORGANISM: Artificial Sequence
<220> FEATURE:
<223> OTHER INFORMATION: Synthetic Construct

<400> SEQUENCE: 6

Met Ser Glu Pro Ala Gly Asp Val Arg Gln Asn Pro Cys Gly Ser Lys
1               5                   10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
        35                  40                  45

Trp Asn Phe Asp Phe Val Thr Glu Thr Pro Leu Glu Gly Asp Phe Ala
    50                  55                  60

Trp Glu Arg Val Arg Gly Leu Gly Leu Pro Lys Leu Tyr Leu Pro Thr
65                  70                  75                  80

Gly Pro Arg Arg Gly Arg Asp Glu Leu Gly Gly Gly Arg Arg Pro Gly
                85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Arg Gln
    130                 135                 140

Thr Ser Met Thr Asp Phe Tyr His Ser Lys Arg Arg Leu Ile Phe Ser
145                 150                 155                 160

Lys Arg Lys Pro Gly Thr Met Thr Ser Lys Val Tyr Asp Pro Glu Gln
                165                 170                 175

Arg Lys Arg Met Ile Thr Gly Pro Gln Trp Trp Ala Arg Cys Lys Gln
            180                 185                 190

Met Asn Val Leu Asp Ser Phe Ile Asn Tyr Tyr Asp Ser Glu Lys His
        195                 200                 205

Ala Glu Asn Ala Val Ile Phe Leu His Gly Asn Ala Ala Ser Ser Tyr
    210                 215                 220

Leu Trp Arg His Val Val Pro His Ile Glu Pro Val Ala Arg Cys Ile
225                 230                 235                 240

Ile Pro Asp Leu Ile Gly Met Gly Lys Ser Gly Lys Ser Gly Asn Gly
                245                 250                 255

Ser Tyr Arg Leu Leu Asp His Tyr Lys Tyr Leu Thr Ala Trp Phe Glu
            260                 265                 270
```

```
Leu Leu Asn Leu Pro Lys Lys Ile Ile Phe Val Gly His Asp Trp Gly
                275                 280                 285

Ala Cys Leu Ala Phe His Tyr Ser Tyr Glu His Gln Asp Lys Ile Lys
290                 295                 300

Ala Ile Val His Ala Glu Ser Val Val Asp Val Ile Glu Ser Trp Asp
305                 310                 315                 320

Glu Trp Pro Asp Ile Glu Glu Asp Ile Ala Leu Ile Lys Ser Glu Glu
                325                 330                 335

Gly Glu Lys Met Val Leu Glu Asn Asn Phe Phe Val Glu Thr Met Leu
                340                 345                 350

Pro Ser Lys Ile Met Arg Lys Leu Glu Pro Glu Glu Phe Ala Ala Tyr
                355                 360                 365

Leu Glu Pro Phe Lys Glu Lys Gly Glu Val Arg Arg Pro Thr Leu Ser
                370                 375                 380

Trp Pro Arg Glu Ile Pro Leu Val Lys Gly Gly Lys Pro Asp Val Val
385                 390                 395                 400

Gln Ile Val Arg Asn Tyr Asn Ala Tyr Leu Arg Ala Ser Asp Asp Leu
                405                 410                 415

Pro Lys Met Phe Ile Glu Ser Asp Pro Gly Phe Phe Ser Asn Ala Ile
                420                 425                 430

Val Glu Gly Ala Lys Lys Phe Pro Asn Thr Glu Phe Val Lys Val Lys
435                 440                 445

Gly Leu His Phe Ser Gln Glu Asp Ala Pro Asp Glu Met Gly Lys Tyr
                450                 455                 460

Ile Lys Ser Phe Val Glu Arg Val Leu Lys Asn Glu Gln
465                 470                 475

<210> SEQ ID NO 7
<211> LENGTH: 2413
<212> TYPE: DNA
<213> ORGANISM: Homo sapiens
<220> FEATURE:
<221> NAME/KEY: CDS
<222> LOCATION: (473)..(1069)

<400> SEQUENCE: 7
cttcttcgtc agcctccctt ccaccgccat attgggccac taaaaaaagg gggctcgtct      60
tttcggggtg ttttttctccc cctccctgt ccccgcttgc tcacggctct gcgactccga    120
cgccggcaag gtttggagag cggctgggtt cgcgggaccc gcgggcttgc acccgcccag    180
actcggacgg gctttgccac cctctccgct tgcctggtcc cctctcctct ccgccctccc    240
gctcgccagt ccatttgatc agcggagact cggcggccgg gccggggctt ccccgcagcc    300
cctgcgcgct cctagagctc gggccgtggc tcgtcgggt ctgtgtcttt tggctccgag    360
ggcagtcgct gggcttccga gaggggttcg ggctgcgtag gggcgctttg ttttgttcgg    420
ttttgttttt ttgagagtgc gagagaggcg gtcgtgcaga cccgggagaa ag atg tca    478
                                                         Met Ser
                                                           1 aac gtg cga gtg tct aac ggg agc cct agc ctg gag cgg atg gac gcc    526
Asn Val Arg Val Ser Asn Gly Ser Pro Ser Leu Glu Arg Met Asp Ala
        5                  10                  15 agg cag gcg gag cac ccc aag ccc tcg gcc tgc agg aac ctc ttc ggc    574
Arg Gln Ala Glu His Pro Lys Pro Ser Ala Cys Arg Asn Leu Phe Gly
 20                  25                  30 ccg gtg gac cac gaa gag tta acc cgg gac ttg gag aag cac tgc aga    622
Pro Val Asp His Glu Glu Leu Thr Arg Asp Leu Glu Lys His Cys Arg
 35                  40                  45                  50
```

```
gac atg gaa gag gcg agc cag cgc aag tgg aat ttc gat ttt cag aat    670
Asp Met Glu Glu Ala Ser Gln Arg Lys Trp Asn Phe Asp Phe Gln Asn
            55                  60                  65 cac aaa ccc cta gag ggc aag tac gag tgg caa gag gtg gag aag ggc    718
His Lys Pro Leu Glu Gly Lys Tyr Glu Trp Gln Glu Val Glu Lys Gly
        70                  75                  80 agc ttg ccc gag ttc tac tac aga ccc ccg cgg ccc ccc aaa ggt gcc    766
Ser Leu Pro Glu Phe Tyr Tyr Arg Pro Pro Arg Pro Pro Lys Gly Ala
            85                  90                  95 tgc aag gtg ccg gcg cag gag agc cag gat gtc agc ggg agc cgc ccg    814
Cys Lys Val Pro Ala Gln Glu Ser Gln Asp Val Ser Gly Ser Arg Pro
        100                 105                 110 gcg gcg cct tta att ggg gct ccg gct aac tct gag gac acg cat ttg    862
Ala Ala Pro Leu Ile Gly Ala Pro Ala Asn Ser Glu Asp Thr His Leu
115                 120                 125                 130 gtg gac cca aag act gat ccg tcg gac agc cag acg ggg tta gcg gag    910
Val Asp Pro Lys Thr Asp Pro Ser Asp Ser Gln Thr Gly Leu Ala Glu
            135                 140                 145 caa tgc gca gga ata agg aag cga cct gca acc gac gat tct tct act    958
Gln Cys Ala Gly Ile Arg Lys Arg Pro Ala Thr Asp Asp Ser Ser Thr
        150                 155                 160 caa aac aaa aga gcc aac aga aca gaa gaa aat gtt tca gac ggt tcc    1006
Gln Asn Lys Arg Ala Asn Arg Thr Glu Glu Asn Val Ser Asp Gly Ser
            165                 170                 175 cca aat gcc ggt tct gtg gag cag acg ccc aag aag cct ggc ctc aga    1054
Pro Asn Ala Gly Ser Val Glu Gln Thr Pro Lys Lys Pro Gly Leu Arg
        180                 185                 190 aga cgt caa acg taa acagctcgaa ttaagaatat gtttccttgt ttatcagata   1109
Arg Arg Gln Thr
195 catcactgct tgatgaagca aggaagatat acatgaaaat tttaaaaata catatcgctg   1169 acttcatgga atggacatcc tgtataagca ctgaaaaaca acaacacaat aacactaaaa   1229 ttttaggcac tcttaaatga tctgcctcta aaagcgttgg atgtagcatt atgcaattag   1289 gttttcctt atttgcttca ttgtactacc tgtgtatata gttttacct tttatgtagc     1349 acataaactt tggggaaggg agggcagggt ggggctgagg aactgacgtg gagcggggta   1409 tgaagagctt gctttgattt acagcaagta gataaatatt tgacttgcat gaagagaagc   1469 aattttgggg aagggtttga attgttttct ttaaagatgt aatgtccctt tcagagacag   1529 ctgatacttc atttaaaaaa atcacaaaaa tttgaacact ggctaaagat aattgctatt   1589 tatttttaca agaagtttat tctcatttgg gagatctggt gatctcccaa gctatctaaa   1649 gtttgttaga tagctgcatg tggcttttttt aaaaaagcaa cagaaaccta tcctcactgc   1709 cctccccagt ctctcttaaa gttggaattt accagttaat tactcagcag aatggtgatc   1769 actccaggta gtttggggca aaaatccgag gtgcttggga gttttgaatg ttaagaattg    1829 accatctgct tttattaaat ttgttgacaa aattttctca ttttcttttc acttcgggct   1889 gtgtaaacac agtcaaaata attctaaatc cctcgatatt tttaaagatc tgtaagtaac   1949 ttcacattaa aaaatgaaat attttttaat ttaaagctta ctctgtccat ttatccacag   2009 gaaagtgtta tttttcaagg aaggttcatg tagagaaaag cacacttgta ggataagtga   2069 aatggatact acatctttaa acagtatttc attgcctgtg tatggaaaaa ccatttgaag   2129 tgtacctgtg tacataactc tgtaaaaaca ctgaaaaatt atactaactt atttatgtta   2189 aaagattttt tttaatctag acaatataca agccaaagtg gcatgttttg tgcatttgta   2249
```

```
aatgctgtgt tgggtagaat aggttttccc ctcttttgtt aaataatatg gctatgctta    2309
aaaggttgca tactgagcca agtataattt tttgtaatgt gtgaaaaaga tgccaattat    2369
tgttacacat taagtaatca ataaagaaaa cttccatagc tatt                     2413

<210> SEQ ID NO 8
<211> LENGTH: 198
<212> TYPE: PRT
<213> ORGANISM: Homo sapiens

<400> SEQUENCE: 8

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Val Glu
65                  70                  75                  80

Lys Gly Ser Leu Pro Glu Phe Tyr Tyr Arg Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
        195

<210> SEQ ID NO 9
<211> LENGTH: 1943
<212> TYPE: DNA
<213> ORGANISM: Homo sapiens
<220> FEATURE:
<221> NAME/KEY: CDS
<222> LOCATION: (277)..(1227)

<400> SEQUENCE: 9
agtgcgctgt gctcgagggg tgccggccag gcctgagcga gcgagctagc cagcaggcat    60
cgagggggcg cggctgccgt ccggacgaga caggcgaacc cgacgcagaa gagtccacca    120
ccggacagcc aggtagccgc cgcgtccctc gcacacgcag agtcgggcgg cgcggggtct    180
cccttgcgcc cggcctccgc cctctcctcc tctcctttcc ccttcttctc gctgtcctct    240
cctctctcgc tgcccgcgtt tgcgcagccc cgggcc atg tcc gac gcg tcc ctc      294
                                      Met Ser Asp Ala Ser Leu
                                       1               5 cgc agc aca tcc acg atg gag cgt ctt gtc gcc cgt ggg acc ttc cca     342
Arg Ser Thr Ser Thr Met Glu Arg Leu Val Ala Arg Gly Thr Phe Pro
        10                  15                  20
```

```
gta cta gtg cgc acc agc gcc tgc cgc agc ctc ttc ggg ccg gtg gac      390
Val Leu Val Arg Thr Ser Ala Cys Arg Ser Leu Phe Gly Pro Val Asp
        25                  30                  35 cac gag gag ctg agc cgc gag ctg cag gcc cgc ctg gcc gag ctg aac      438
His Glu Glu Leu Ser Arg Glu Leu Gln Ala Arg Leu Ala Glu Leu Asn
    40                  45                  50 gcc gag gac cag aac cgc tgg gat tac gac ttc cag cag gac atg ccg      486
Ala Glu Asp Gln Asn Arg Trp Asp Tyr Asp Phe Gln Gln Asp Met Pro
55                  60                  65                  70 ctg cgg ggc cct gga cgc ctg cag tgg acc gaa gtg gac agc gac tcg      534
Leu Arg Gly Pro Gly Arg Leu Gln Trp Thr Glu Val Asp Ser Asp Ser
                75                  80                  85 gtg ccc gcg ttc tac cgc gag acg gtg cag gtg ggg cgc tgc cgc ctg      582
Val Pro Ala Phe Tyr Arg Glu Thr Val Gln Val Gly Arg Cys Arg Leu
            90                  95                  100 ctg ctg gcg ccg cgg ccc gtc gcg gtc gcg gtg gct gtc agc ccg ccc      630
Leu Leu Ala Pro Arg Pro Val Ala Val Ala Val Ala Val Ser Pro Pro
        105                 110                 115 ctc gag ccg gcc gct gag tcc ctc gac ggc ctc gag gag gcg ccg gag      678
Leu Glu Pro Ala Ala Glu Ser Leu Asp Gly Leu Glu Glu Ala Pro Glu
    120                 125                 130 cag ctg cct agt gtc ccg gtc ccg gcc ccg gcg tcc acc ccg ccc cca      726
Gln Leu Pro Ser Val Pro Val Pro Ala Pro Ala Ser Thr Pro Pro Pro
135                 140                 145                 150 gtc ccg gtc ctg gct cca gcc ccg gcc ccg gct ccg gct ccg gtc gcg      774
Val Pro Val Leu Ala Pro Ala Pro Ala Pro Ala Pro Ala Pro Val Ala
                155                 160                 165 gct ccg gtc gcg gct ccg gtc gcg gtc gcg gtc ctg gcc ccg gcc ccg      822
Ala Pro Val Ala Ala Pro Val Ala Val Ala Val Leu Ala Pro Ala Pro
            170                 175                 180 gcc ccg gct ccg gct ccg gct ccg gcc ccg gct cca gtc gcg gcc ccg      870
Ala Pro Ala Pro Ala Pro Ala Pro Ala Pro Ala Pro Val Ala Ala Pro
        185                 190                 195 gcc cca gcc ccg gcc ccg gcc ccg gcc ccg gcc ccc gcc ccg gcc ccg      918
Ala Pro Ala Pro Ala Pro Ala Pro Ala Pro Ala Pro Ala Pro Ala Pro
    200                 205                 210 gcc ccg gac gcg gcg cct caa gag agc gcc gag cag ggc gcg aac cag      966
Ala Pro Asp Ala Ala Pro Gln Glu Ser Ala Glu Gln Gly Ala Asn Gln
215                 220                 225                 230 ggg cag cgc ggc cag gag cct ctc gct gac cag ctg cac tcg ggg att     1014
Gly Gln Arg Gly Gln Glu Pro Leu Ala Asp Gln Leu His Ser Gly Ile
                235                 240                 245 tcg gga cgt ccc gcg gcc ggc acc gcg gcc gcc agc gcc aac ggc gcg     1062
Ser Gly Arg Pro Ala Ala Gly Thr Ala Ala Ala Ser Ala Asn Gly Ala
            250                 255                 260 gcg atc aag aag ctg tcc ggg cct ctg atc tcc gat ttc ttc gcc aag     1110
Ala Ile Lys Lys Leu Ser Gly Pro Leu Ile Ser Asp Phe Phe Ala Lys
        265                 270                 275 cgc aag aga tca gcg cct gag aag tcg tcg ggc gat gtc ccc gcg ccg     1158
Arg Lys Arg Ser Ala Pro Glu Lys Ser Ser Gly Asp Val Pro Ala Pro
    280                 285                 290 tgt ccc tct cca agc gcc gcc cct ggc gtg ggc tcg gtg gag cag acc     1206
Cys Pro Ser Pro Ser Ala Ala Pro Gly Val Gly Ser Val Glu Gln Thr
295                 300                 305                 310 ccg cgc aag agg ctg cgg tga gccaatttag agcccaaaga gccccgaggg         1257
Pro Arg Lys Arg Leu Arg
                315 aacctgccgg ggcagcggac gttggaaggg cgctgggcct cggctgggac cgttcatgta    1317
```

-continued

```
gcagcaaccg gcggcggctg ccgcagagca gcgttcggtt ttgttttaa attttgaaaa   1377
ctgtgcaatg tattaataac gtcttttat atctaaatgt attctgcacg agaaggtaca   1437
ctggtcccaa ggtgtaaagc tttaagagtc atttatataa aatgtttaat ctctgctgaa   1497
actcagtgca aaaaaagaa aaagaaaaa aaaaggaaa aataaaaaa accatgtata    1557
tttgtacaaa aagttttaa agttatacta acttatattt tctatttatg tccaggcgtg   1617
gaccgctctg ccacgcacta gctcggttat tggttatgcc aaaggcactc tccatctccc   1677
acatctggtt attgacaagt gtaactttat tttcatcgcg gactctgggg aagggggtca   1737
ctcacaagct gtagctgcca tacatgccca tctagcttgc agtctcttcg cgctttcgct   1797
gtctctctta ttatgactgt gtttatctga aacttgaaga caagtctgtt aaaatggttc   1857
ctgagccgtc tgtaccactg ccccggcccc tcgtccgccg ggttctaaat aaagaggccg   1917
aaaaatgctg caaaaaaaaa aaaaaa                                       1943
```

<210> SEQ ID NO 10
<211> LENGTH: 316
<212> TYPE: PRT
<213> ORGANISM: Homo sapiens

<400> SEQUENCE: 10

```
Met Ser Asp Ala Ser Leu Arg Ser Thr Ser Thr Met Glu Arg Leu Val
1               5                   10                  15
Ala Arg Gly Thr Phe Pro Val Leu Val Arg Thr Ser Ala Cys Arg Ser
            20                  25                  30
Leu Phe Gly Pro Val Asp His Glu Glu Leu Ser Arg Glu Leu Gln Ala
        35                  40                  45
Arg Leu Ala Glu Leu Asn Ala Glu Asp Gln Asn Arg Trp Asp Tyr Asp
    50                  55                  60
Phe Gln Gln Asp Met Pro Leu Arg Gly Pro Gly Arg Leu Gln Trp Thr
65                  70                  75                  80
Glu Val Asp Ser Asp Ser Val Pro Ala Phe Tyr Arg Glu Thr Val Gln
                85                  90                  95
Val Gly Arg Cys Arg Leu Leu Leu Ala Pro Arg Pro Val Ala Val Ala
            100                 105                 110
Val Ala Val Ser Pro Pro Leu Glu Pro Ala Ala Glu Ser Leu Asp Gly
        115                 120                 125
Leu Glu Glu Ala Pro Glu Gln Leu Pro Ser Val Pro Val Pro Ala Pro
    130                 135                 140
Ala Ser Thr Pro Pro Pro Val Pro Val Leu Ala Pro Ala Pro Ala Pro
145                 150                 155                 160
Ala Pro Ala Pro Val Ala Ala Pro Val Ala Pro Val Ala Val Ala
            165                 170                 175
Val Leu Ala Pro Ala Pro Ala Pro Ala Pro Ala Pro Ala Pro Ala Pro
        180                 185                 190
Ala Pro Val Ala Ala Pro Ala Pro Ala Pro Ala Pro Ala Pro Ala Pro
    195                 200                 205
Ala Pro Ala Pro Ala Pro Ala Pro Asp Ala Ala Pro Gln Glu Ser Ala
    210                 215                 220
Glu Gln Gly Ala Asn Gly Gln Arg Gly Gln Pro Leu Ala Asp
225                 230                 235                 240
Gln Leu His Ser Gly Ile Ser Gly Arg Pro Ala Ala Gly Thr Ala Ala
                245                 250                 255
Ala Ser Ala Asn Gly Ala Ala Ile Lys Lys Leu Ser Gly Pro Leu Ile
```

```
                260                 265                 270
Ser Asp Phe Phe Ala Lys Arg Lys Arg Ser Ala Pro Glu Lys Ser Ser
        275                 280                 285

Gly Asp Val Pro Ala Pro Cys Pro Ser Pro Ser Ala Ala Pro Gly Val
    290                 295                 300

Gly Ser Val Glu Gln Thr Pro Arg Lys Arg Leu Arg
305                 310                 315
```

ASSAY FOR INHIBITORS OF CIP/KIP PROTEIN DEGRADATION

CROSS-REFERENCE TO RELATED APPLICATIONS

This application is a National Entry Application of PCT application no PCT/CA2012/050682 filed on Sep. 28, 2012 and published in English under PCT Article 21(2), which itself claims benefit of U.S. provisional application Ser. No. 61/540,151, filed on Sep. 28, 2011. All documents above are incorporated herein by reference in their entirety.

TECHNICAL FIELD

The present generally concerns assays, and more particularly to screening assays and systems for the identification of inhibitors of p21 degradation.

SEQUENCE LISTING

Pursuant to 37 C.F.R. 1.821(c), a sequence listing is submitted herewith as an ASCII compliant text file named "15691_47- sequence listing_ST25.txt", created on Sep. 28, 2012 and having a size of ~42 kilobytes. The content of the aforementioned file is hereby incorporated by reference in its entirety.

BACKGROUND ART

The Cell Cycle as a Therapeutic Target for Cancer

Progression through the cell division cycle is controlled by oscillating waves of Cdk activity (1). These kinases are regulated positively by association with cyclin subunits and negatively by binding to Cdk inhibitors (2, 3). The Ubiquitin-Proteasome System (UPS) (FIG. 1) plays a key role in controlling cell cycle progression by promoting the periodic degradation of cyclins and Cdk inhibitors (4, 5).

Deregulation of cell cycle progression is a hallmark of human cancer (6). Although Cdks are rarely mutated in cancer, their activity is universally deregulated owing to hyperactivation of upstream signaling pathways (Ras-MAP kinase, PI 3-kinase), amplification of Cdk or cyclin genes, genetic/epigenetic inactivation of Ink4 Cdk inhibitors, or downregulation of p21 and p27 Cdk inhibitors (7-9). For example, cyclin D1 is overexpressed in several tumors as a result of transcriptional activation, gene amplification, or translocation. $p16^{Ink4a}$ a is frequently inactivated by gene deletion, point mutation or epigenetic silencing, resulting in activation of cyclin D-dependent kinases. Aberrant activation of Cdk2 and Cdk1 is observed in various malignancies. Other protein kinases such as Aurora A/B and Plk1, which are involved in centrosome duplication and mitosis execution, are overexpressed in a wide range of tumor types (10, 11). In addition to cell cycle kinases, deregulation of the mechanisms that control protein stability has been shown to contribute to tumorigenesis. Overexpression of oncogenic E3 ligases (such as Skp2), which target negative regulators of the cell cycle, or inactivation of tumor suppressor E3 ligases like Fbxw7 is observed in many human tumors (4, 5, 12).

Since it was established that aberrant cell cycle control is a hallmark of cancer, development of agents targeting the cell cycle has been viewed as a promising strategy for cancer therapy. For more than a decade, there has been an intensive search for small molecules that target Cdks, but no Cdk inhibitor drug has yet been approved for clinical use (7, 13, 14). More recent efforts have focused on the development of inhibitors for Aurora and Polo kinases (15-17). However, further investigation is necessary to assess the clinical potential of these targets. On the other hand, the FDA approval of the proteasome inhibitor bortezomib (Velcade; Millenium) for the treatment of multiple myeloma in 2003 (18) has heralded an entirely new class of cancer drugs and validated the therapeutic potential of the UPS (12, 19-22).

The Cip/Kip Family of Cdk Inhibitors

The activity of Cdks is negatively regulated by Cdk inhibitors. In human, 7 Cdk inhibitors have been identified and classified into two families, according to structural and functional similarities (1, 23). The Ink4 proteins, which include $p16^{Ink4A}$, $p15^{Ink4B}$, $p18^{Ink4C}$ and $p19^{INK4D}$ contain multiple ankyrin repeats and interact specifically with Cdk4 and Cdk6 to inactivate cyclin D-Cdk complexes. Members of the Cip/Kip family, which is composed of p21, p27 and p57, inhibit all cyclin-Cdk complexes and are not specific to a particular cell cycle phase. Structurally, the three Cip/Kip proteins share a conserved domain at their N-terminus, consisting of two separable subdomains for binding to cyclin and Cdk subunits (FIG. 2). They also have a nuclear localization signal (NLS) near the C-terminus. Notably, p21 also contains a proliferating cell nuclear antigen (PCNA) binding domain.

Biochemical and genetic analyses indicate that p21, p27 and p57 have both overlapping and specific cellular functions. p21 is a transcriptional target of p53 and is believed to be one of the main effectors of p53-mediated cell cycle arrest (24). The p21 protein is expressed ubiquitously in adult tissues. In the developing embryo, the expression of p21 correlates with terminal differentiation of a variety of tissues such as skeletal and heart muscle, cartilage and skin (25, 26). These observations implicated p21 in the regulation of cell cycle withdrawal during terminal differentiation. p27 is expressed ubiquitously and act as a negative regulator of cell proliferation in a variety of cell types (26). Accordingly, the expression of p27 is high in quiescent cells and in cells exposed to anti-proliferative signals, and declines in response to mitogenic factor stimulation (27-29). p57 is highly expressed in the developing embryo, but its expression declines in adults (26).

Regulation of p21 Expression in Normal and Cancer Cells

The regulation of p21 protein is exerted at multiple levels. The amount of p21 is controlled mainly at the levels of transcription and protein turnover (30). p21 was originally identified as the product of a gene activated by p53 (31). Since then, a variety of cellular and viral factors have been shown to induce or repress p21 transcription by p53-independent mechanisms (30, 32). In cancer cells, repression of p21 gene transcription is associated either with loss of function of activators (p53) or upregulation or gain of function mutations of transcriptional repressors. For example, the Myc oncogene is a potent repressor of p21 transcription (33). Importantly, p21 is a very unstable protein that is degraded by the proteasome (FIG. 3). Four E3 ubiquitin ligase complexes, $SCF^{skp2}$ (34), $CRL4^{cdt2}$ (35-37), $APC/C^{Cdc20}$ (38) and MKRN1 (39) have been shown to promote the degradation of p21 at specific stages of the cell cycle. Several proteins involved in the ubiquitin-dependent proteolysis of p21 are upregulated in a variety of human tumours, indicating that p21 downregulation may account for the oncogenic properties of these proteins. For example, Skp2, the substrate binding subunit of the $SCF^{skp2}$ E3 ligase, is frequently upregulated in human cancers and displays oncogenic properties (4). Similarly, Cdt2 and Cul4a, two subunits of the CRL4$^{cdt2}$ E3 ligase are overexpressed in breast and advanced liver cancers (40-43).

p21 is a Potent Tumor Suppressor

Mouse genetic studies and human clinical investigations have provided compelling evidence that p21 is a bona fide tumor suppressor. Mice deficient in p21 develop tumours of hematopoietic, endothelial and epithelial origin with late onset (44). Furthermore, p21 deficiency accelerates the development of chemically induced tumors in mice (45-47) and cooperates with oncogenes to promote tumorigenesis (48). Importantly, two recent studies have shown that knock-in mice expressing the p53 R172P mutant, that is deficient for apoptosis but maintains its ability to induce p21 and cell cycle arrest, are able to suppress tumorigenesis in different cancer models (49, 50). Tumor suppression by this p53 mutant was modulated by p21, which induced senescence and preserved chromosomal stability. p21 is not a classical tumor suppressor gene as it is very rarely mutated in human tumors. However, p21 levels are frequently downregulated in human cancers (including carcinomas, gliomas and hematological malignancies) and this is usually associated with a poor prognosis (30, 51). As mentioned above, downregulation of p21 is most often associated with increased turnover of the protein.

Accumulating evidence suggest that p21 exerts its tumor suppressor activity through multiple mechanisms. In addition to its ability to inhibit cyclin-Cdks and induce cell cycle arrest, microarray-based studies indicate that p21 expression is associated with the suppression of genes important for cell cycle progression and the induction of senescence genes (52). Interestingly, recent work suggests that tumor regression can be achieved through the reactivation of senescence, by restoring p53 function (53) or by inactivation of Myc in tumors with functional p53 (54). Reactivation of p53 and Myc inactivation both leads to p21 upregulation. p21 can compete for PCNA binding with several PCNA-reliant proteins involved in DNA repair processes (55). Finally, p21 has been reported to either inhibit or promote apoptosis depending on the cellular context (30). Interestingly, a recent study showed that p21 promotes apoptosis of intestinal stem/progenitor cells in response to gamma irradiation, suggesting that increasing p21 expression may be a viable approach to selectively target colon cancer stem cells (56).

There is thus a need for the development of novel strategies to inhibit p21 degradation, such as novel methods and assays to identify inhibitors of p21 degradation.

The present description refers to a number of documents, the content of which is herein incorporated by reference in their entirety.

SUMMARY OF THE INVENTION

In a first aspect, the present invention provides a high throughput Screening (HTS)-compatible method for determining whether a test compound may be useful for treating cancer, said method comprising (a) contacting said test compound with a cell expressing a fusion protein in the presence of a protein synthesis inhibitor, said fusion protein comprising (i) a Cip/Kip polypeptide; and (i) a reporter protein linked to the C-terminal of said Cip/Kip polypeptide, wherein said fusion protein has a half-life that is similar to that of said Cip/Kip polypeptide, and (b) measuring a readout signal from the reporter protein, wherein a higher readout signal from the reporter protein in the presence of said test compound, relative to the readout signal in the absence of said test compound, is indicative that said test compound may be useful for treating cancer.

In another aspect, the present invention provides a high throughput Screening (HTS)-compatible system for determining whether a test compound may be useful for treating cancer, said system comprising:
 a cell expressing a fusion protein, said fusion protein comprising (i) a Cip/Kip polypeptide; and (i) a reporter protein linked to the C-terminal of said Cip/Kip polypeptide, wherein said fusion protein has a half-life that is similar to that of said Cip/Kip polypeptide;
 a protein synthesis inhibitor; and
 a detection system to measure the readout signal from the reporter protein.

In an embodiment, the above-mentioned half-life is about 1 hour or less, in a further embodiment the half-life is from 30 minutes to about 1 hour.

In an embodiment, the above-mentioned protein synthesis inhibitor is cycloheximide (CHX).

In an embodiment, the above-mentioned said reporter protein is a luciferase, in a further embodiment *Renilla* luciferase. In a further embodiment, the *Renilla* luciferase is a polypeptide comprising the amino acid sequence of SEQ ID NO:4, or a functional variant or fragment thereof having *Renilla* luciferase activity. In yet a further embodiment, the *Renilla* luciferase is a polypeptide comprising the amino acid sequence of SEQ ID NO:4.

In an embodiment, the above-mentioned readout signal from the reporter protein is bioluminescence in the presence of a luciferase substrate. In a further embodiment, the luciferase substrate is coelenterazine or an analog thereof.

In an embodiment, the above-mentioned the Cip/Kip polypeptide is a p21 polypeptide, in a further embodiment a polypeptide comprising the amino acid sequence of SEQ ID NO:2, or a functional variant or fragment thereof having p21 activity. In a further embodiment, the p21 polypeptide is a polypeptide comprising the amino acid sequence of SEQ ID NO:2.

In an embodiment, the above-mentioned cell further comprises an inducible expression system for inducible expression of the fusion protein. In a further embodiment, the above-mentioned inducible expression system is a tetracycline-controlled expression system.

In an embodiment, the nucleic acid encoding said fusion protein is operably linked to tetracycline-responsive elements (TREs).

In an embodiment, the above-mentioned cell further expresses a reverse tetracycline-responsive transcriptional activator (rtTA).

In an embodiment, the above-mentioned method further comprises contacting said cell with tetracycline (Tc), or an analog thereof, in a further embodiment the Tc analog is doxycycline (Dox).

In an embodiment, the above-mentioned cell is a fibroblast, in a further embodiment a Rat1 cell.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 5A shows a schematic representation of the p21-Renilla luciferase (Rluc) reporter construct. FIG. 5B shows an immunoblot analysis of the degradation rate of Rluc and p21-Rluc fusion protein upon addition of CHX in the presence or absence of the proteasome inhibitor MG 132. A specific antibody to Rluc was used for detection. FIG. 5C shows a quantification of the data in FIG. 5B expressed as relative abundance;

FIG. 10A shows a dose-response curve of the effect of the proteasome inhibitor MG132 and an inactive compound X in the p21-Rluc assay. Luciferase values are normalized to the control DMSO (set to 1). FIG. 10B shows a dose-response curve of MG132 and compound X using a p21 ELISA assay to measure the expression of endogenous p21 protein. ELISA values are normalized to the control DMSO.

FIG. 11A shows the nucleotide sequence of human p21 mRNA (transcript variant 1, NCBI Reference Sequence: NM_000389.4, SEQ ID NO:1), with the coding sequence in italics (nucleotides 126-620);

FIG. 11B shows the amino acid sequence of human p21 protein (NCBI Reference Sequence: NP_000380.1, SEQ ID NO:2);

FIG. 12A shows the nucleotide sequence of *Renilla reniformis* luciferase mRNA (GenBank: M63501.1, SEQ ID NO:3), with the coding sequence in italics (nucleotides 10-945);

FIG. 12B shows the amino acid sequence of *Renilla reniformis* luciferase (GenBank: AAA29804.1, SEQ ID NO:4);

FIG. 13 shows the nucleotide (SEQ ID NO:5) and amino acid (SEQ ID NO:6) sequences of the p21-Rluc fusion construct used in the experiments described herein. The construct comprises a "linker" (highlighted in grey) corresponding to a KpnI restriction site (used to prepare the fusion construct) between p21 and Rluc, which results in the presence of 2 amino acids (Gly and Thr) between the two proteins in the fusion;

FIG. 14A shows the nucleotide sequence of human p27 mRNA (NCBI Reference Sequence: NM_004064.3, SEQ ID NO:7), with the coding sequence in italics;

FIG. 14B shows the amino acid sequence of human p27 protein (NCBI Reference Sequence: NP_004055.1, SEQ ID NO:8);

FIG. 15A shows the nucleotide sequence of human p57 mRNA (NCBI Reference Sequence: NM_000076.2, SEQ ID NO:9), with the coding sequence in italics;

FIG. 15B shows the amino acid sequence of human p57 protein (NCBI Reference Sequence: NP_000067.1, SEQ ID NO:10).

DISCLOSURE OF INVENTION

Figure 1:
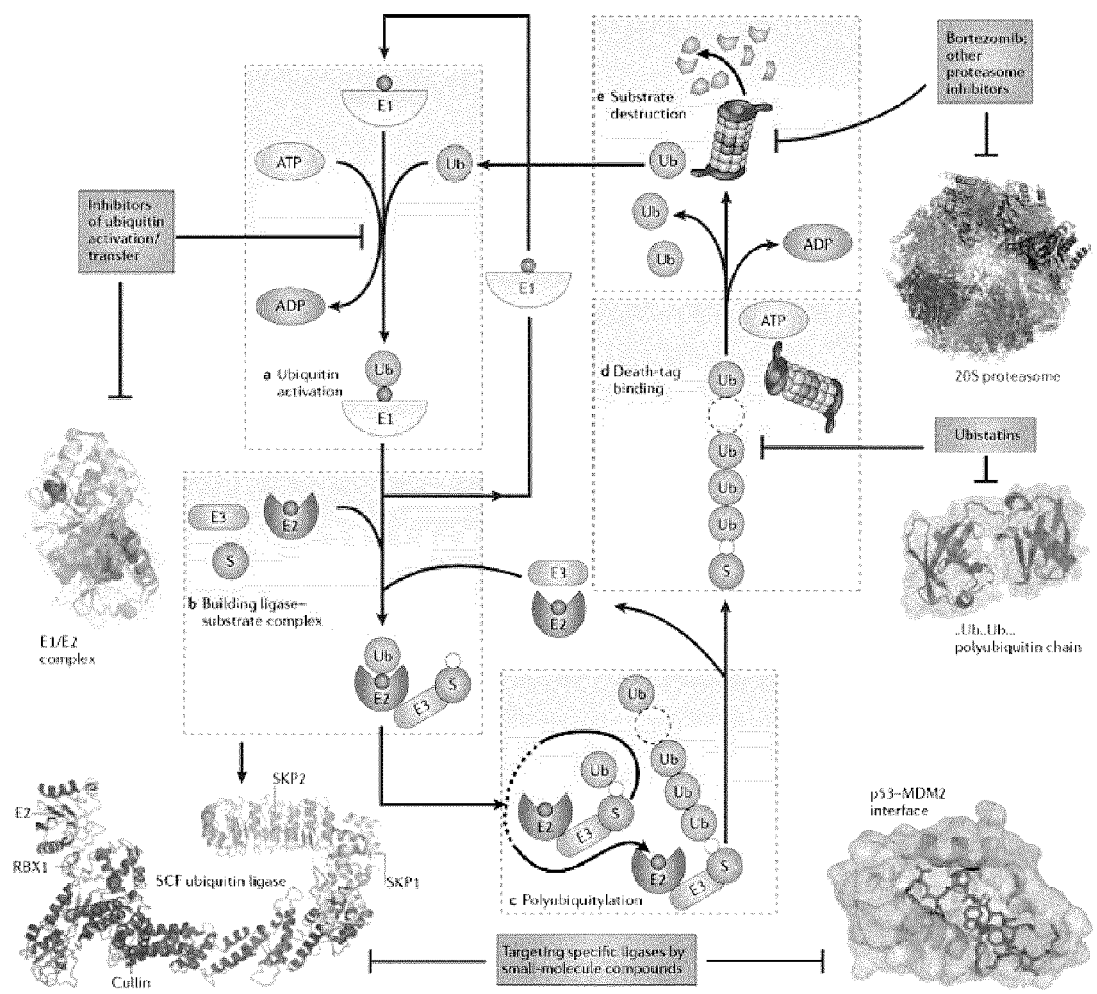
FIG. 1 shows an overview of the Ubiquitin-Proteasome System (UPS)
Figure 2:
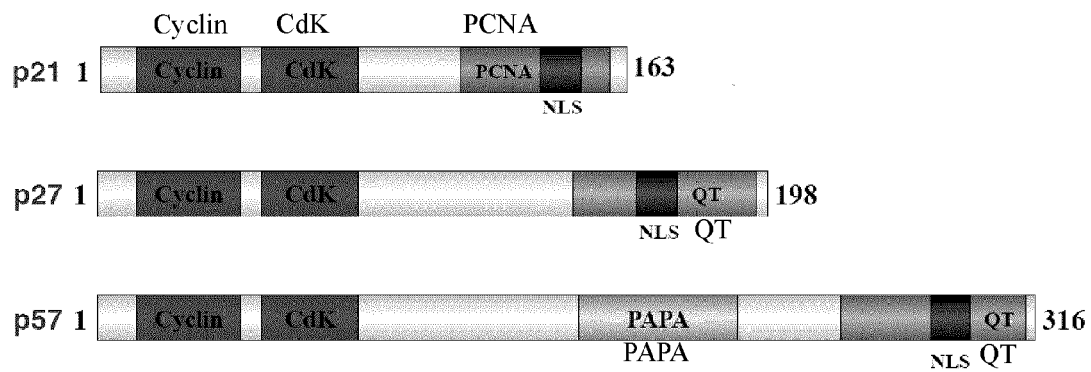
FIG. 2 shows a schematic representation of the human Cip/Kip family of Cdk inhibitors.
Figure 3:
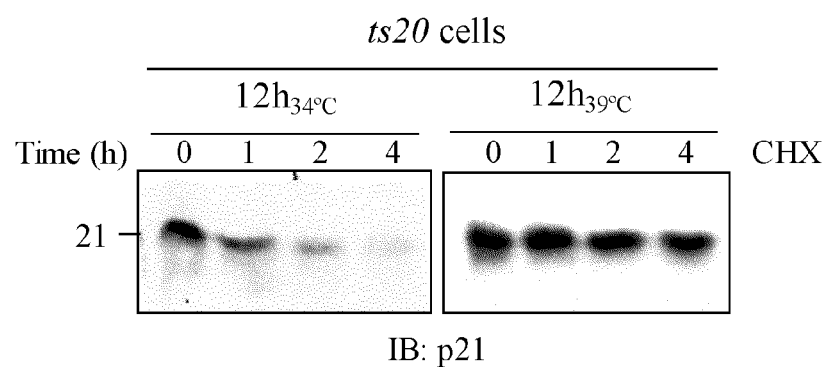
FIG. 3 shows that p21 is an unstable protein degraded by the UPS. ts20 cells, which bear a temperature-sensitive mutation in the E1 enzyme, were incubated at the permissive (34° C., E1 active) or non-permissive (39° C., E1 inactive) temperature and treated with the protein synthesis inhibitor cycloheximide (CHX) for different times. Expression of p21 was measured by immunoblotting
Figure 4:
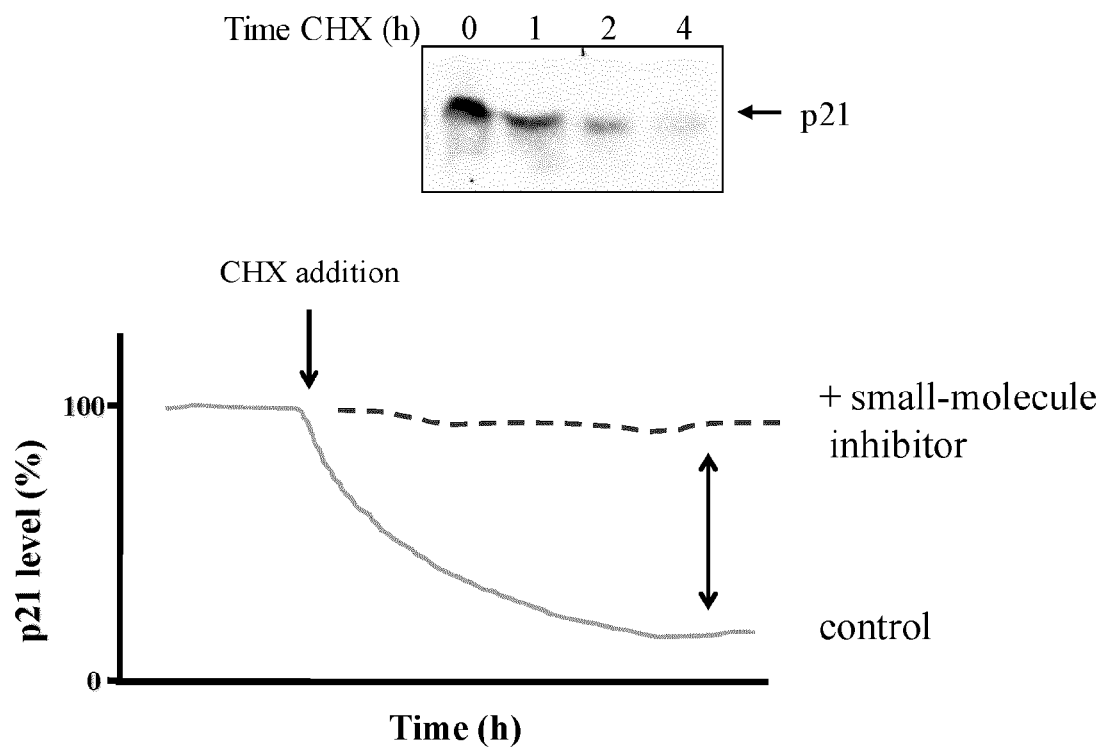
FIG. 4 shows the underlying principle of the p21 degradation assay. p21 is an unstable protein with an half-life of about 30-60 minutes. Upon addition of CHX to block protein synthesis, the p21 protein is rapidly degraded. Addition of a small molecule inhibitor of p21 degradation is predicted to stabilize p21 leading to its accumulation in the cells.

An assay compatible with high-throughput screening (HTS) that is capable of identifying inhibitors, such as small-molecule inhibitors, of the degradation of the Cdk inhibitor of the Cip/Kip family (e.g., p21), was designed. Inhibitors identified by this assay may be useful to inhibit the proliferation of tumor cells, and thus for the treatment of cancers. Accordingly, in a first aspect, the present invention provides a high throughput screening (HTS)-compatible method for determining whether a test compound may be useful for treating cancer, said method comprising (a) contacting said test compound with a cell expressing a fusion protein in the presence of a protein synthesis inhibitor, said fusion protein comprising a reporter protein fused to the C-terminal end of a Cip/Kip polypeptide, wherein said fusion protein has a half-life that is similar to that of said Cip/Kip polypeptide, and (b) determining a readout signal from the reporter protein, wherein a higher readout signal from the reporter protein in the presence of said test compound, relative to the readout signal in the absence of said test compound, is indicative that said test compound may be useful for treating cancer.

In another aspect, the present invention provides a high throughput screening (HTS)-compatible method for determining whether a test compound may be useful for (i) inhibiting (e.g., preventing, decreasing) Cip/Kip protein degradation, (ii) stabilizing Cip/Kip protein expression, and/or (iii) inducing the cellular accumulation of Cip/Kip protein, said method comprising (a) contacting said test compound with a cell expressing a fusion protein in the presence of a protein synthesis inhibitor, said fusion protein comprising a reporter protein fused to the C-terminal end of a Cip/Kip polypeptide, wherein said fusion protein has a half-life that is similar to that of said Cip/Kip polypeptide, and (b) determining a readout signal from the reporter protein, wherein a higher readout signal from the reporter protein in the presence of said test compound, relative to the readout signal in the absence of said test compound, is indicative that said test compound may be useful for inhibiting (e.g., preventing, decreasing) Cip/Kip degradation (or stabilization of Cip/Kip expression).

In another aspect, the present invention provides a high throughput screening (HTS)-compatible method for determining whether a test compound may be useful for inhibiting cell growth arrest and/or cell cycle progression, said method comprising (a) contacting said test compound with a cell expressing a fusion protein in the presence of a protein synthesis inhibitor, said fusion protein comprising a reporter protein fused to the C-terminal end of a Cip/Kip polypeptide, wherein said fusion protein has a half-life that is similar to that of said Cip/Kip polypeptide, and (b) determining a readout signal from the reporter protein, wherein a higher readout signal from the reporter protein in the presence of said test compound, relative to the readout signal in the absence of said test compound, is indicative that said test compound may be useful for inhibiting cell growth arrest, and/or cell cycle progression.

In another aspect, the present invention provides a high throughput screening (HTS)-compatible system for determining whether a test compound may be useful for treating cancer, said system comprising:

a cell expressing a fusion protein, said fusion protein comprising (i) a Cip/Kip polypeptide; and (i) a reporter protein linked to the C-terminal of said Cip/Kip polypeptide, wherein said fusion protein has a half-life that is similar to that of said Cip/Kip polypeptide;

a protein synthesis inhibitor;

a detection system to measure the readout signal from the reporter protein.

In another aspect, the present invention provides a high throughput screening (HTS)-compatible system for determining whether a test compound may be useful for (i) inhibiting (e.g., preventing, decreasing) Cip/Kip protein degradation, (ii) stabilizing Cip/Kip protein expression, and/or (iii) inducing the cellular accumulation of Cip/Kip protein, said system comprising:

a cell expressing a fusion protein, said fusion protein comprising (i) a Cip/Kip polypeptide; and (i) a reporter protein linked to the C-terminal of said Cip/Kip polypeptide, wherein said fusion protein has a half-life that is similar to that of said Cip/Kip polypeptide;

a protein synthesis inhibitor;

a detection system to measure the readout signal from the reporter protein.

In another aspect, the present invention provides a high throughput screening (HTS)-compatible system for determining whether a test compound may be useful for inhibiting cell growth arrest and/or cell cycle progression, said system comprising:

a cell expressing a fusion protein, said fusion protein comprising (i) a Cip/Kip polypeptide; and (i) a reporter protein linked to the C-terminal of said Cip/Kip polypeptide, wherein said fusion protein has a half-life that is similar to that of said Cip/Kip polypeptide;

a protein synthesis inhibitor;

a detection system to measure the readout signal from the reporter protein.

The term "high-throughput screening" (HTS) as used herein refers to a method that allow screening rapidly and in parallel large numbers of compounds (hundreds, thousands) for binding activity or biological activity against target molecules. Such HTS methods are typically performed in microtiter plates having several wells, for example 384, 1536, or 3456 wells. For HTS, it is important that the readout signal be detected with high sensitivity, accuracy and reproducibility.

The above-mentioned fusion protein has a half-life that is similar to that of said Cip/Kip (e.g., p21) polypeptide. In an embodiment, the half-life is the half-life within a cell, for example a cell cultured in vitro, in petri culture dishes. "Similar" as used in that context means that the difference between the half-life of the fusion protein and a Cip/Kip (e.g., p21) polypeptide (alone, not in the fusion protein), under the same conditions (e.g., same cells, same culture conditions) is less than 25%, in further embodiments less than 20, 15 or 10%. In an embodiment, the half-life of said fusion protein is about 1 hour or less, in a further embodiment between about 30 minutes to about 1 hour. Methods to measure the half-life of proteins are well known in the art. In embodiments, the half-life of the fusion protein may be measured using the cycloheximide chase and p21 immunoblotting analysis described below.

The term "reporter protein" refers to a protein that can be detected (e.g., by fluorescence, spectroscopy, luminometry, etc.) easily and that is not present normally (endogenously) in the system used. Commonly used reporter proteins include enzymes such as β-galactosidase (encoded by the bacterial gene IacZ), luciferase, chloramphenyl acetyltransferase (CAT; from bacteria), GUS (β-glucuronidase), bioluminescent proteins and fluorescent proteins. In the context of the present invention, the reporter protein is selected so as to not significantly affect the half-life of Cip/Kip (e.g., p21), i.e. so that the Cip/Kip-reporter protein fusion has a half-life that is similar to that of the Cip/Kip (e.g., p21) polypeptide alone. The skilled person would be able to easily determine the suitable reporter proteins for the above-noted methods/systems by measuring the half-life of a fusion protein comprising Cip/Kip (e.g., p21) and the reporter protein, and comparing it to the half-like of Cip/Kip (e.g., p21). In an embodiment, the reporter protein is a luciferase. The term luciferase refers to a class of oxidative enzymes used in bioluminescence. Many luciferases are known in the art, for example firefly luciferase (for example from the firefly *Photinus pyralis*), *Renilla* luciferase (*Renilla reniformis*), *Metridia* luciferase (MetLuc, derived from the marine copepod Metridia longa), *Aequorea* luciferase, Dinoflagellate luciferase, or *Gaussia* luciferase (Gluc). In an embodiment, the luciferase is a *Renilla* luciferase. In an embodiment, the *Renilla* luciferase is a polypeptide comprising the amino acid sequence of SEQ ID NO:4 (FIG. 12B), or a functional variant or fragment thereof having *Renilla* luciferase activity. *Renilla* Luciferase activity as used herein refers to the ability to metabolize the substrate coelenterazine (6-(4-hydroxyphenyl)-2-[(4-hydroxphenylmethyl]-8-(phenylmethyl)-7H-imidazo[3,2-a]pyrazin-3-one). In an embodiment, the functional variant or fragment comprises a sequence having at least 70% identity with the sequence of SEQ ID NO:4 (FIG. 12B). In further embodiments, the functional variant or fragment comprises a sequence having at least 75, 80, 85, 90, 95, 96, 97, 98 or 99% identity with the sequence of SEQ ID NO:4 (FIG. 12B). In an embodiment, when an enzyme is used as the reporter protein, the above-mentioned method further comprises contacting the cell with a substrate of the enzyme so as to induce the production of a detectable metabolite. In an embodiment, when the reporter protein is a *Renilla* luciferase, the above-mentioned method further comprises contacting the cell with coelenterazine or an analog thereof, which catalyzes coelenterazine oxidation by oxygen to produce light. Coelenterazine and several coelenterazine analogs (coelenterazine cp, f, h, hcp, fcp, i, ip, n, 400a, methyl Coelenterazine) are commercially available from Life Technologies™, Molecular Probes™ and Biotium™, for example (see also, e.g., Zhao et al., *Mol Imaging*, 2004 3(1):43-54). In a further embodiment, the just-noted contacting the cell with coelenterazine or an analog thereof is for a period of about 1 to about 10 minutes, for example about 3 to about 7 minutes, more specifically about 5 minutes.

The method to determine the readout signal from the reporter protein depends from the nature of the reporter protein. For example, for fluorescent reporter proteins, the readout signal corresponds to the intensity of the fluorescent signal. The readout signal may be measured using spectroscopy-, fluorometry-, photometry-, and/or luminometry-based methods and detection systems, for example. Such methods and detection systems are well known in the art.

The term "Cip/Kip polypeptide" refers to a cyclin-dependent kinase (CDK) inhibitors of the Cip/Kip family and includes the protein p21, p27 and p57. The nucleotide and amino acid sequences of p21, p27 and p57 are depicted in FIGS. 11A-11B, 14A-14B and 15A-15B, respectively. In an embodiment, the Cip/Kip polypeptide is a polypeptide comprising the amino acid sequence of SEQ ID NO:2, 8 or 10 (FIG. 11B, 14B or 15B), or a functional variant or fragment thereof having the activity of native p21, p27 or p57 (e.g., inhibition of CDK, regulation of cell cycle progression). In an embodiment, the functional variant or fragment comprises a sequence having at least 70% identity with the sequence of SEQ ID NO:2, 8 or 10 (FIG. 11B, 14B or 15B). In further embodiments, the functional variant or fragment comprises a sequence having at least 75, 80, 85, 90, 95, 96, 97, 98 or 99% identity with the sequence of SEQ ID NO:2, 8 or 10 (FIG. 11B, 14B or 15B).

In an embodiment, the Cip/Kip polypeptide is a p21 polypeptide. The term "p21 polypeptide" refers to a polypeptide that inhibits cyclin-dependent kinase (CDK) and regulates cell cycle progression. The sequences of p21 polypeptides from various organisms and species are known in the art, for example mouse: NCBI Reference Sequence NP_001104569.1; Rat: GenBank AAC52221.1; cow: NCBI Reference Sequence NP_001092428.1; human: NCBI Reference Sequence NP_000380.1, SEQ ID NO:2 (FIG. 11B). In an embodiment, the p21 polypeptide is a polypeptide comprising the amino acid sequence of SEQ ID NO:2 (FIG. 11B), or a functional variant or fragment thereof having the activity of native p21 (e.g., inhibition of CDK, regulation of cell cycle progression). In an embodiment, the functional variant or fragment comprises a sequence having at least 70% identity with the sequence of SEQ ID NO:2 (FIG. 11B). In further embodiments, the functional variant or fragment comprises a sequence having at least 75, 80, 85, 90, 95, 96, 97, 98 or 99% identity with the sequence of SEQ ID NO:2 (FIG. 11B).

The term "protein synthesis inhibitor" refers to an agent that blocks/inhibits the processes that lead to the generation of new proteins. Such agents usually act at the ribosome level. In an embodiment, the protein synthesis inhibitor is a eukaryotic protein synthesis inhibitor. Examples of eukaryotic protein synthesis inhibitors include cycloheximide (CHX), puromycin, isomigrastatin, lactimidomycin (LTM), Actinomycin D, Anisomycin, emetine, and analogs thereof. In an embodiment, the protein synthesis inhibitor is cycloheximide (CHX).

In embodiments, the Cip/Kip (e.g., p21) polypeptide may be covalently linked to the reporter protein either directly (e.g., through a peptide bond) or via a suitable linker moiety, e.g., a linker of one or more amino acids (e.g., a polyglycine linker) or another type of chemical linker (e.g., a carbohydrate linker, a lipid linker, a fatty acid linker, a polyether linker, PEG, etc. (see, e.g., Hermanson (1996) Bioconjugate techniques). In an embodiment, the Cip/Kip (e.g., p21) polypeptide and the reporter protein are covalently linked through a peptide bond. In an embodiment, the p21 polypeptide and the reporter protein are covalently linked through a linker, in a further embodiment a 2-amino acid linker. In a further embodiment, the linker comprises a glycine residue and a threonine residue. In a further embodiment, the fusion protein comprises the amino acid sequence of SEQ ID NO:6 (FIG. 13).

In an embodiment, the above-mentioned reporter protein is under inducible expression. Accordingly, in another embodiment, the cell further comprises an inducible expression system.

In a further embodiment, the inducible expression system is a tetracycline-controlled/regulated expression system. Inducible expression systems, such as tetracycline-controlled/regulated expression systems, are well known in the art and are commercially available. Examples of such systems include the RheoSwitch® Mammalian Inducible Expression System from New England BioLabs Inc., Tet-Express™ Inducible Expression Systems from Clontech, and the T-REx™ System from Life Technologies.

In an embodiment, the nucleic acid sequence encoding the above-mentioned fusion protein is operably linked to inducible transcriptional regulatory element sequence(s). A nucleic acid sequence is "operably-linked" with a second nucleic acid sequence when the first nucleic acid sequence is placed in a functional relationship with the second nucleic acid. For instance, a promoter is operably-linked to a coding sequence if the promoter affects the transcription or expression of the coding sequences. Generally, operably-linked DNA sequences are contiguous and, where necessary to join two protein coding regions, in reading frame. However, since, for example, enhancers generally function when separated from the promoters by several kilobases and intronic sequences may be of variable lengths, some polynucleotide elements may be operably-linked but not contiguous. "Transcriptional regulatory element sequence(s)" is a generic term that refers to DNA sequences, such as initiation and termination signals, enhancers, and promoters, splicing signals, polyadenylation signals which induce or control transcription of protein coding sequences with which they are operably-linked. In an embodiment, the transcriptional regulatory element sequences are tetracycline-responsive elements (TREs). The tetracycline response elements consist of 7 repeats of the 19 bp bacterial tet-o sequence separated by spacer sequences.

In an embodiment, the above-mentioned cell further expresses a tetracycline-responsive transcriptional activator (tTA, Tet-Off expression system), or a reverse tetracycline-responsive transcriptional activator (rtTA, Tet-On expression system).

A tetracycline transactivator (tTA) protein is a fusion of the TetR (tetracycline repressor), found in *Escherichia coli* bacteria with another protein, VP16, produced by Herpes Simplex Virus (HPV). In the absence of tetracycline (Tc) or an analog thereof (doxycycline, Dox), tTA binds to the TRE and activates transcription of the target gene. In the presence of Tc or Dox, which binds tTA, tTA is not capable of binding to TRE sequences, thereby preventing transactivation of target genes (the nucleic acid encoding the fusion protein).

A reverse tetracycline-responsive transcriptional activator (rtTA) is also a fusion protein comprised of the TetR repressor and the VP16 transactivation domain; however, a four amino acid change in the tetR DNA binding moiety alters rtTA's binding characteristics such that it can only recognize the tetO sequences in the TRE of the target transgene in the presence of tetracycline or an analog thereof (doxycycline, Dox). Thus, in such as a system, transcription of the TRE-regulated target gene is stimulated by rtTA only in the presence of tetracycline or an analog thereof.

In an embodiment, the above-mentioned cell further expresses a reverse tetracycline-responsive transcriptional activator (rtTA, Tet-On expression system). In an embodiment, the method further comprises culturing the cell in the presence of tetracycline (Tc), or an analog thereof, to induce the expression of the fusion protein by the cell. In a further embodiment, the tetracycline (Tc) derivative is doxycycline (Dox).

In another embodiment, the above-mentioned method comprises:

(a1) contacting the cell expressing the fusion protein with tetracycline or a tetracycline analog to induce the expression of the fusion protein;

(b1) contacting the test compound with the cell of (a) in the presence of a protein synthesis inhibitor; and (c1) determining a readout signal from the reporter protein.

In an embodiment, the above contacting at step (a1) is for a period of from about 8 to about 30 hours, for example from about 12 to about 24 hours, more specifically about 18 hours.

In an embodiment, the above contacting at step (b1) is for a period of from about 2 to about 10 hours, for example from about 4 to about 8 hours, more specifically about 6 hours.

Any cell capable of expressing the fusion protein may be used in the method/system of the invention. In an embodiment, the above-mentioned cell is a mammalian cell (e.g., animal cell, mouse cell, rat cell, human cell). In a further embodiment, the cell is a cell line, in a further embodiment a fibroblast cell line, in yet a further embodiment a rat cell line. In yet a further embodiment, the cell is a Rat1 cell.

The cell may be prepared by introducing a nucleic acid encoding the above-mentioned fusion protein (by any transfection, transduction or transformation method), such as the nucleic acid comprising the sequence of SEQ ID NO:6, and providing conditions suitable for the expression of the fusion protein. Methods and systems for introducing a nucleic acid into a cell are well known in the art, and include for example chemical-based transfection (using calcium phosphate, liposomes, cationic polymers such as DEAE-dextran or polyethylenimine), electroporation, gene gun, viral transduction. Kits for introducing a nucleic acid into a cell are commercially available.

In an embodiment, the above-mentioned cancer is a cancer associated with a decrease expression, or downregulated levels, of p21, p27 and/or p57 (reviewed in references 30, 51 and 67, for example). In a further embodiment, the above-mentioned cancer is a cancer associated with a decrease expression, or downregulated levels, of p21. In an embodiment, the above-mentioned cancer is a human cancer, in further embodiments a carcinoma, glioma or hematological malignancy (e.g., leukemia). In an embodiment, the cancer is a breast, gastrointestinal (e.g., gastric, colon), liver, tonsillar ovarian, cervical, pancreatic, laryngeal or oral cancer. p57(Kip2) protein is frequently downregulated in different types of human epithelial and nonepithelial cancers as a consequence of genetic and epigenetic events (67). Accordingly, in another embodiment, the cancer is an epithelial or nonepithelial cancer.

Test compounds (drug candidates) that may be screened by the method/system of the invention may be obtained from any number of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means.

In another aspect, the present invention provides a fusion protein as defined above, or a nucleic acid encoding such fusion protein, or a cell comprising the fusion protein or nucleic acid encoding same.

In another aspect, the present invention provides a kit comprising the fusion protein defined above, or a nucleic acid encoding such fusion protein, or a cell comprising the fusion protein or nucleic acid encoding same. In embodiments, the kit further comprises one or more of the components of the system defined above, as well as instructions for performing the HTS-compatible method defined above.

MODE(S) FOR CARRYING OUT THE INVENTION

The present invention is illustrated in further details by the following non-limiting examples.

EXAMPLE 1

Materials and Methods

Generation of p21-Rluc Protein Fusion

The human p21Cip1 (p21) and *Renilla* luciferase (Rluc) genes were amplified by polymerase chain reaction (PCR) from plasmids pRmHa-5 HA-p21Cip1 and pcDNA3.1-Rluc respectively. PCR products were digested and ligated into a modified version of pRevTRE vector (Clonetech) previously digested with BamHI and NotI restriction enzymes. The final recombinant molecules (pRevTRE Rluc and pRevTRE-p21-Rluc) were sequenced to ensure the integrity of DNA.

Generation of Rat1 rtTA Stable Cell Line

Human Embryonic Kidney 293T cells were transfected with pCL-Eco and pRevTet-On vectors in order to produce retroviral particle bearing the reverse tet-transactivator transgene (rtTA). Rat1 cells were infected with these retroviruses and selected with G418 for 2 weeks to generate the Rat1 rtTA cell line.

Generation of Rat-1 rtTA Inducible Rluc/p21-Rluc Stable Cell Lines

Human Embryonic Kidney 293T cells were transfected with pCL-Eco in combination with either pRevTRE Rluc of pRevTRE p21-Rluc to produce retroviral particles. Rat1 rtTA cells were infected with these retroviruses in the presence of 10 ug/ml polybrene. Cells were selected with hygromycin B and G418 for 5 days to generate Rat1 rtTA Rluc and Rat1 rtTA p21-Rluc cell lines.

High Throughput p21 Degradation Assay

Stable cell lines from frozen vials were thawed and resuspended in phenol red-free DMEM (Wisent) supplemented with 10% NBCS (day 0). Two days after, cells were trypsinized and seeded at 2500 cells/well into white 384-well plates (BD Bioscience). Doxycyclin was added at 1 µg/ml into the culture medium in order to induce the expression of Rluc and/or p21-Rluc (day 2). Cells were incubated at 37° C. for 18 h. On day 3, 5 µl of cycloheximide was added into each well to reach a final concentration of 50 µg/ml. The proteasome inhibitor MG132 was added into few wells on each plate as positive control at a final concentration of 25 µM. Dimethyl sulfoxide (DMSO) was added into few wells on each plate as negative control. Compounds were pre-diluted in water and 5 µl of the diluted solutions was added at a final concentration of 10 µM. The final volume in each well was 50 µl and the final concentration of DMSO through the whole screen was 0.5%. Plates were incubated at 37° C. for 6 h. Culture medium was then aspirated and 50 µl of a solution containing the *Renilla* luciferase substrate coelenterazine was added at a final concentration of 5 µM. The reaction was allowed to proceed for 5 minutes and luminescence was monitored using EnVision™ plate reader (Perkin Elmer) set to "Enhanced luminescence" mode.

EXAMPLE 2

High-throughput Screening (HTS)-compatible Cell-based Assay

Figure 5A:
FIGS. 5A-C show the design and basis of the p21 degradation reporter assay.

To identify small molecules that lead to an increase in the expression levels of p21, a highly robust HTS-compatible cell-based assay using a reporter protein made of a fusion between the unstable p21 protein and *Renilla luciferase* (p21-Rluc) was designed. The assay relies on the generation of a fusion protein between p21 and a reporter protein that is quantifiable in a high throughput format. The genetically engineered chimeric protein should behave like the wild type p21 protein, such that the readout signal from the reporter moiety will reflect the regulation of p21. Two fusions proteins were initially constructed: a fusion between p21 and the *Renilla* luciferase (p21-Rluc) and a fusion between p21 and the GFP protein (p21-GFP) (FIG. 5A)

Luciferase activity is detected by measuring bioluminescence after addition of coelenterazine to intact cells, whereas GFP expression is measured by fluorescence spectroscopy. The two fusion constructs were stably expressed in a fibroblast cell line using an inducible Tet-On retroviral expression system. Since p21 is a negative regulator of the cell cycle, the use of an inducible vector permits to repress its expression and allows the amplification and maintenance of the transduced cell lines.

Figure 5B:
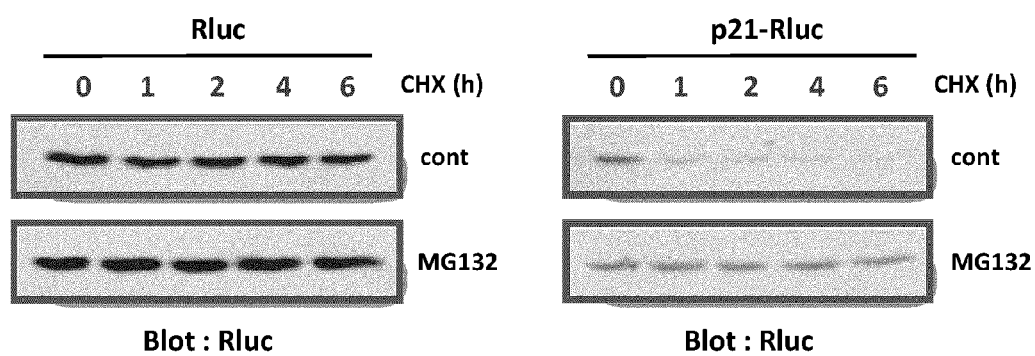
Figure 5C:
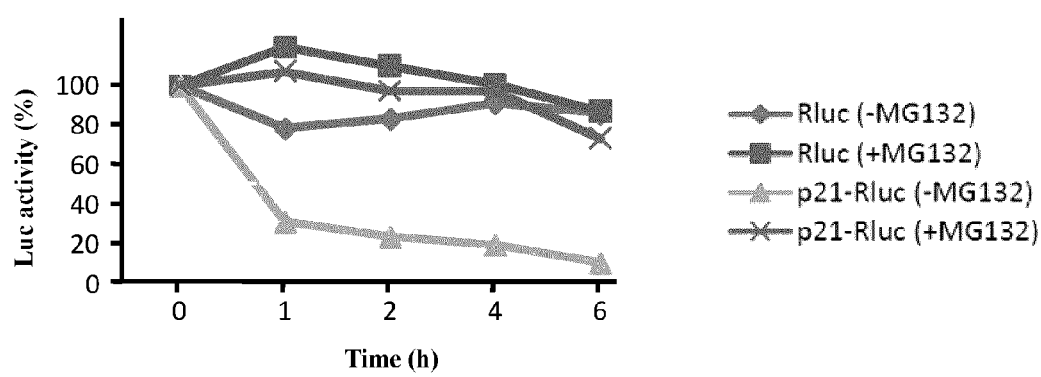

To validate the assay, expression of the p21 fusion protein was induced with the tetracycline derivative doxycycline and the protein synthesis inhibitor cycloheximide was added to stop new protein synthesis. The rate of degradation of the p21 fusion was then measured by cycloheximide chase and immunoblotting analysis with a *Renilla* luciferase-specific antibody (US Biological, Catalog #L6003-20). The proteasome inhibitor MG-132 was used as control to confirm that the degradation was proteasome-dependent. The fusion of GFP to p21 was found to artificially stabilize the p21 protein and this strategy was not pursued further. In contrast, the p21-Rluc protein was found to be highly unstable with a half-life of less than 1 hour, comparable to that of the wild type p21 protein (FIG. 5B). However, the Rluc-p21 fusion protein (i.e. in which the Rluc is N-terminal relative to p21) was found to artificially stabilize the p21 protein. To ascertain that the degradation rate of p21-Rluc reflects the half-life of p21, the same assay was used to monitor the degradation of Rluc alone. No degradation of Rluc was observed under these conditions, consistent with the reported stability of the *Renilla* luciferase protein (FIG. 5C). From these results, it may be concluded that the stability of the p21-Rluc fusion protein is a true reflection of the stability of p21 and that the construct can be used in a cell-based assay for screening purposes.

Figure 6:
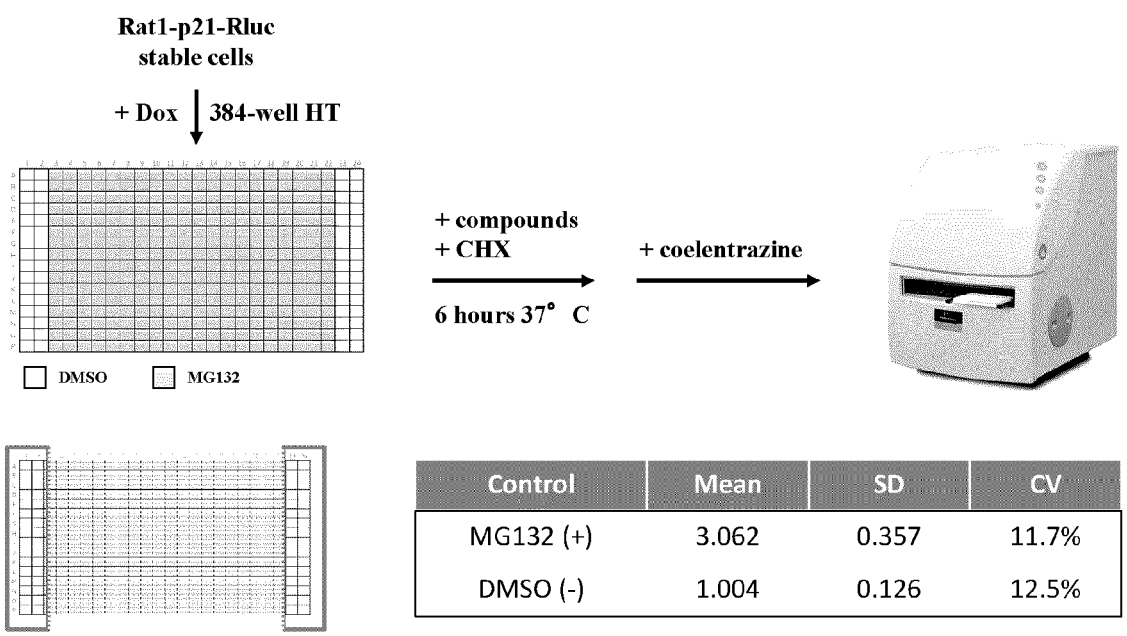
FIG. 6 shows a schematic representation of the HTS assay in 384-well plates used to screen a library of small molecule compounds using the p21-Rluc reporter assay described herein.
Figure 7:
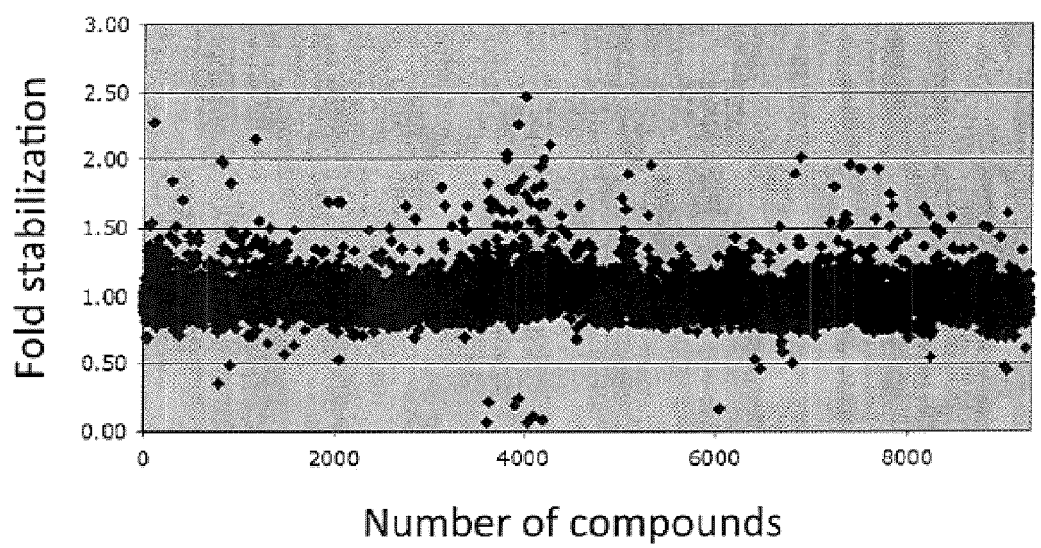
FIG. 7 shows (A) the results expressed as fold stabilization values for one HTS run representing 9,984 small molecule compounds. (B) Distribution of the fold stabilization data for the 112,900 compounds tested in the primary screen using the p21-Rluc reporter assay described herein.
Figure 7:
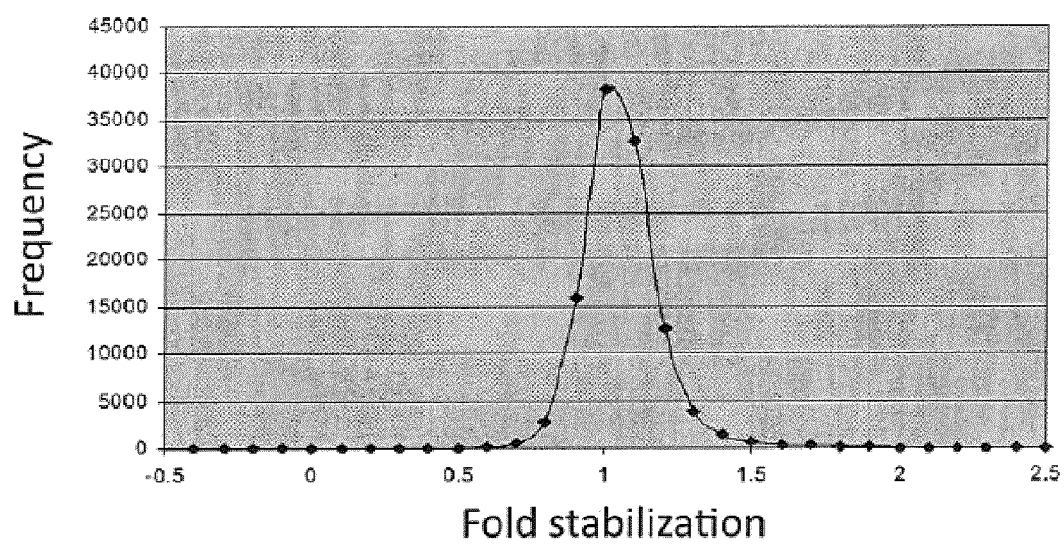
Figure 8:
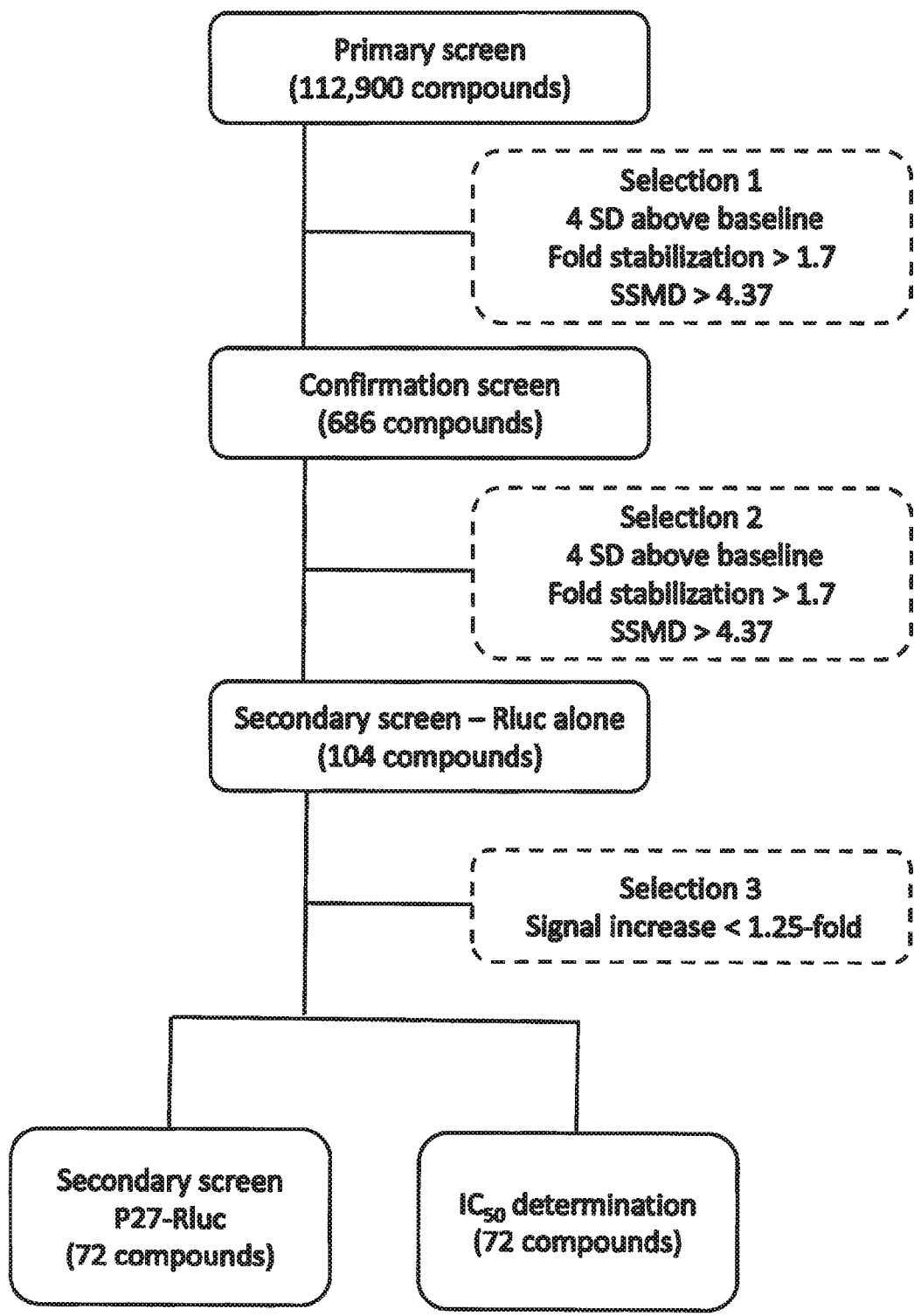
FIG. 8 shows a summary of the screen and decision tree showing the different assays implemented and the corresponding statistical methods applied for hits selection. The number of compounds tested at each step is indicated.
Figure 9:
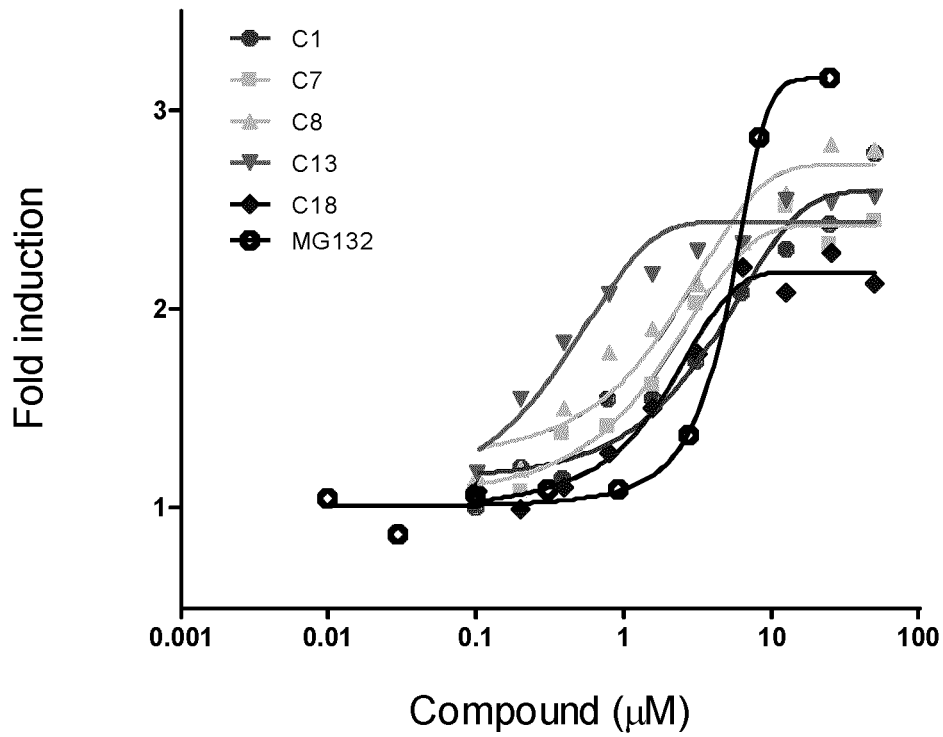
FIG. 9 shows dose-response curves of selected compounds identified from the primary screen using the p21-Rluc reporter assay. The proteasome inhibitor MG132 was used as control.
Figure 10A:
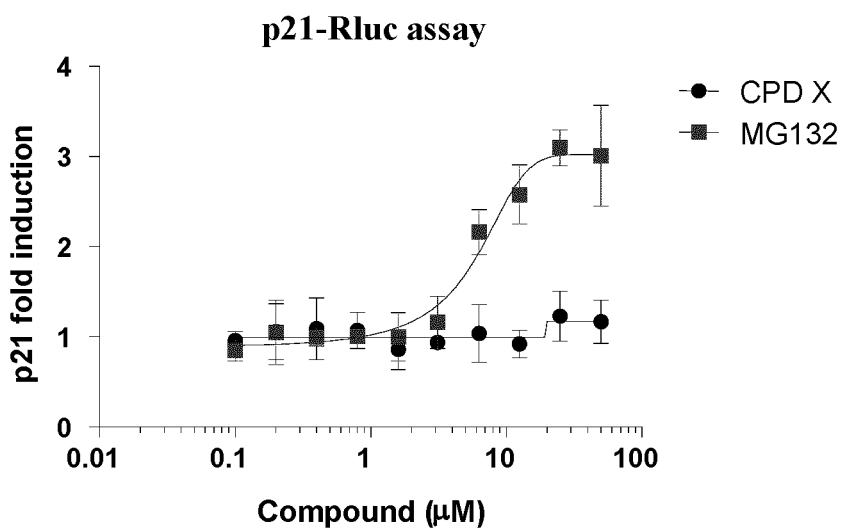
FIGS. 10A and 10B shows the validation of the p21-Rluc reporter assay by ELISA.
Figure 10B:
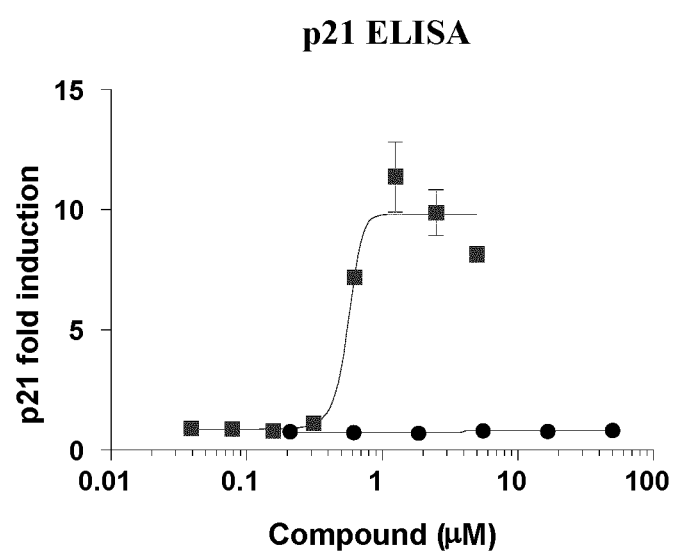

The p21-Rluc degradation assay was next transposed to a HTS-compatible format in 384-well plates and used to screen the Institut de Recherche en Immunologie et Cancerologie's (IRIC's) collection of 112,900 compounds (FIG. 6) derived from the Chembridge DIVERset™ screening library, the Maybridge Hitfinder™ screening library, the Specs screening library, the Microsource SPECTRUM™ collection, the Biomol/Enzo Life Sciences Screen-Well™ library, the Prestwick Chemical Library™ library and the Sigma LOPAC$^{1280}$™. The potent proteasome inhibitor MG-132 was used as positive control. The mean increase of p21-Rluc signal by all positive controls across the screen was 3.062 (FIG. 6). This value was set at 100% stabilization and used as comparison reference for test compounds. From the primary screen, 686 compounds that increase the p21-Rluc luminescence signal by at least 1.7-fold and 4 SDs above baseline (DMSO control) were identified (FIG. 5). These compounds were re-tested in a reconfirmation experiment using the same assay conditions. A subset of 104 molecules was confirmed to be active by applying the same statistical criteria. Confirmed hits were then tested in a secondary assay using Rluc alone to eliminate compounds that increase luciferase enzymatic activity or boost the luminescence signal. From this assay, 72 molecules were selected for further evaluation. These molecules were tested in secondary screens using p27-Rluc and ERK3-Rluc fusion proteins to determine if they specifically inhibit p21 degradation or if they also block the degradation of p27 and the unrelated protein kinase ERK3, which would suggest that the molecules target the proteasome. Dose-response curves were generated for all compounds to estimate $IC_{50}$ values. FIG. 9 shows a representative example of dose-response curves for a subset of active hit compounds identified in the assay. Interestingly, from the 72 molecules selected, 14 were found to inhibit the degradation of both p21 and p27 by more than 60% compared to the reference MG-132. Another 4 compounds inhibited p21 degradation by more than 60% but had less than 25% inhibitory effect on p27 proteolysis. None of these molecules had a significant effect on ERK3 degradation. Ten molecules had $ED_{50}$ values in the low μM range. The screening data for these molecules are summarized in Table 1A and 1B. These hit compounds were re-synthesized and their biological activity was confirmed in the p21 degradation assay. To validate that the increase in luciferase activity of the p21-Rluc fusion protein truly reflects an increase in the expression of the endogenous p21 protein, we have developed a p21 ELISA to measure its abundance. As shown in FIG. 10 for the MG132 control and an inactive molecule, the increase in luciferase activity reflected an increase in the intracellular expression of the endogenous protein. The same correlation was observed for the positive hits identified in the screen.

TABLE 1A

List of potential inhibitors of p21 and p27 degradation
Threshold p21 > 60%
Threshold p27 > 60%

| | Primary screen | | | Secondary screen | | | | |
|---|---|---|---|---|---|---|---|---|
| | Primary screen (Fold stabilization) | Primary screen (SSMD) | Confirmation (Fold stabilization) | Rluc (Fold stabilization) | Anisomycine (Fold stabilization) | Secondary screen p21-Rluc (% stabilization) | Secondary screen p27-Rluc (% stabilization) | $IC_{50}$ (μM) |
| UM1 | 2.24 | 6.85 | 2.27 | 1.04 | 2.69 | 84.83 | 83.61 | 6.30 |
| UM2 | 2.28 | 9.83 | 2.36 | 0.84 | 2.71 | 93.86 | 89.88 | 3.04 |
| UM3 | 2.00 | 6.57 | 2.23 | 0.84 | 2.06 | 71.27 | 74.62 | 4.61 |
| UM4 | 2.26 | 7.70 | 2.52 | 1.05 | 1.98 | 68.41 | 72.74 | >20.00 |

TABLE 1A-continued

List of potential inhibitors of p21 and p27 degradation
Threshold p21 > 60%
Threshold p27 > 60%

|  | Primary screen | | | Secondary screen | | | | |
|---|---|---|---|---|---|---|---|---|
|  | Primary screen (Fold stabilization) | Primary screen (SSMD) | Confirmation (Fold stabilization) | Rluc (Fold stabilization) | Anisomycine (Fold stabilization) | Secondary screen p21-Rluc (% stabilization) | Secondary screen p27-Rluc (% stabilization) | IC$_{50}$ (µM) |
| UM5 | 2.20 | 9.47 | 2.46 | 1.19 | 2.80 | 97.53 | 66.88 | 1.11 |
| UM6 | 1.93 | 5.62 | 2.49 | 1.18 | 3.10 | 98.35 | 68.60 | 1.04 |
| UM7 | 2.10 | 5.66 | 2.19 | 0.86 | 2.10 | 68.99 | 89.22 | 4.84 |
| UM8 | 2.28 | 7.11 | 2.09 | 0.98 | 2.68 | 70.88 | 75.45 | >20.00 |
| UM9 | 2.32 | 9.85 | 2.24 | 1.02 | 2.50 | 87.13 | 89.74 | 12.02 |
| UM10 | 1.84 | 4.91 | 2.10 | 1.12 | 2.79 | 74.28 | 82.27 | 0.83 |
| UM11 | 2.54 | 7.70 | 2.83 | 0.78 | 2.10 | 78.06 | 74.91 | 2.07 |
| UM12 | 2.60 | 10.89 | 2.18 | 1.01 | 2.87 | 78.16 | 73.30 | 0.76 |
| UM13 | 2.15 | 8.05 | 2.54 | 1.19 | 2.57 | 68.59 | 61.23 | 1.83 |
| UM14 | 1.83 | 5.01 | 2.16 | 1.11 | 2.26 | 63.67 | 61.44 | 8.37 |

TABLE 1B

List of potential specific inhibitors of p21 degradation
Threshold p21 > 60%
Threshold p27 < 25%

|  | Primary screen | | | Secondary screen | | | | |
|---|---|---|---|---|---|---|---|---|
|  | Primary screen (Fold stabilization) | Primary screen (SSMD) | Confirmation (Fold stabilization) | Rluc (Fold stabilization) | Anisomycine (Fold stabilization) | Secondary screen p21-Rluc (% stabilization) | Secondary screen p27-Rluc (% stabilization) | IC$_{50}$ (µM) |
| UM15 | 2.10 | 10.04 | 2.20 | 0.96 | 2.70 | 62.31 | 18.35 | 3.41 |
| UM16 | 1.87 | 6.80 | 2.07 | 1.06 | 2.56 | 62.61 | 4.18 | >20.00 |
| UM17 | 1.68 | 5.62 | 2.41 | 1.08 | 2.64 | 60.94 | 13.14 | >20.00 |
| UM18 | 1.89 | 5.27 | 2.20 | 1.03 | 2.53 | 67.32 | 23.44 | 1.89 |

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", an and the include corresponding plural references unless the context clearly dictates otherwise.

REFERENCES

1. Morgan, D. O. 2007. The cell cycle: principles of control. London, UK: New Science Press Ltd.
2. Malumbres, M., and Barbacid, M. 2005. Mammalian cyclin-dependent kinases. Trends Biochem Sci 30:630-641.
3. Sherr, C. J., and Roberts, J. M. 1999. CDK inhibitors: positive and negative regulators of G1-phase progression. Genes Dev 13:1501-1512.
4. Frescas, D., and Pagano, M. 2008. Deregulated proteolysis by the F-box proteins SKP2 and beta-TrCP: tipping the scales of cancer. Nat Rev Cancer 8:438-449.
5. Nakayama, K. I., and Nakayama, K. 2006. Ubiquitin ligases: cell-cycle control and cancer. Nat Rev Cancer 6:369-381.
6. Hanahan, D., and Weinberg, R A. 2000. The hallmarks of cancer. Cell 100:57-70.
7. Lapenna, S., and Giordano, A. 2009. Cell cycle kinases as therapeutic targets for cancer. Nat Rev Drug Discov 8:547-566.
8. Malumbres, M., and Barbacid, M. 2009. Cell cycle, CDKs and cancer: a changing paradigm. Nat Rev Cancer 9:153-166.
9. Ortega, S., Malumbres, M., and Barbacid, M. 2002. Cyclin D-dependent kinases, INK4 inhibitors and cancer. Biochim Biophys Acta 1602:73-87.
10. Marumoto, T., Zhang, D., and Saya, H.2005. Aurora-A—a guardian of poles. Nat Rev Cancer 5:42-50.
11. Takai, N., Hamanaka, R, Yoshimatsu, J., and Miyakawa, 1. 2005. Polo-like kinases (Plks) and cancer. Oncogene 24:287-291.
12. Kitagawa, K., Kotake, Y., and Kitagawa, M. 2009. Ubiquitin-mediated control of oncogene and tumor suppressor gene products. Cancer Sci 100:1374-1381.
13. Malumbres, M., Pevarello, P., Barbacid, M., and Bischoff, J.R 2008. CDK inhibitors in cancer therapy: what is next? Trends Pharmacol Sei 29: 16-21.
14. Shapiro, G.I. 2006. Cyclin-dependent kinase pathways as targets for cancer treatment. J Clin Oncol 24: 1770-1783.
15. Keen, N., and Taylor, S. 2004. Aurora-kinase inhibitors as anticancer agents. Nat Rev Cancer 4:927-936.
16. Perez de Castro, I., de Career, G., Montoya, G., and Malumbres, M. 2008. Emerging cancer therapeutic opportunities by inhibiting mitotic kinases. Curr Opin Pharmacol 8:375-383.

17. Strebhardt, K., and Ullrich, A. 2006. Targeting polo-like kinase 1 for cancer therapy. Nat Rev Cancer 6:321-330.
18. Adams, J. 2004. The proteasome: a suitable antineoplastic target. Nat Rev Cancer 4:349-360.
19. Cardozo, T., and Pagano, M. 2007. Wrenches in the works: drug discovery targeting the SCF ubiquitin ligase and APC/C complexes. BMC Biochem 8 Suppl 1:S9.
20. Hoeller, D., and Dikic, I. 2009. Targetingthe ubiquitin system in cancer therapy. Nature 458:438-444.
21. Nalepa, G., Rolfe, M., and Harper, J.W. 2006. Drug discovery in the ubiquitinproteasome system. Nat Rev Drug Discov 5:596-613.
22. Sterz, J., von Metzler, L, Hahne, J.C., Lamottke, B., Rademacher, J., Heider, U., Terpos, E., and Sezer, 0. 2008. The potential of proteasome inhibitors in cancer therapy. Expert Opin Investig Drugs 17:879-895.
23. Sherr, C.J., and Roberts, J.M. 1995. Inhibitors of mammalian G1 cyclin-dependent kinases. Genes Dev 9:1149-1163.
24. Vogelstein, B., Lane, D., and Levine, A J. 2000. Surfing the p53 network. Nature 408:307-310.
25. Ciemerych, M.A, and Sicinski, P. 2005. Cell cycle in mouse development. Oncogene 24:2877-2898.
26. Nakayama, K. 1998. Cip/Kip cyclin-dependent kinase inhibitors: brakes of the cell cycle engine during development. Bioassays 20: 1020-1 029.
27. Coats, S., Flanagan, W.M., Nourse, J., and Roberts, J.M. 1996. Requirement of $p27_{KiP1}$ for restriction point control of the fibroblasts cell cycle. Science 272:877880.
28. Nourse, J., Firpo, E, Flanagan, W.M., Coats, S., Polyak, K., Lee, M.H., Massague, J., Crabtree, G.R, and Roberts, J.M. 1994. Interleukin-2-mediated elimination of the $p27_{KiP1}$ cyclin-dependent kinase inhibitor prevented by rapamycin. Nature 372:570-573.
29. Servant, M.J., Coulombe, P., Turgeon, B., and Meloche, S. 2000. Differential regulation of p27(Kip1) expression by mitogenic and hypertrophie factors: Involvement of transcriptional and posttranscriptional mechanisms. J Cell Biol 148:543-556.
30. Abbas, T, and Dutta, A 2009. p21 in cancer: intricate networks and multiple activities. Nat Rev Cancer 9:400-414.
31. el-Deiry, W.S., Tokino, T, Velculescu, V.E, Levy, D.B., Parsons, R, Trent, J.M., Lin, D., Mercer, W.E, Kinzler, K.W., and Vogelstein, B. 1993. WAF1, a potential mediator of p53 tumor suppression. Cell 75:817-825.
32. Gartel, AL., and Radhakrishnan, S.K. 2005. Lost in transcription: p21 repression, mechanisms, and consequences. Cancer Res 65:3980-3985.
33. Cotler, H.A, Grandori, C., Tamayo, P., Colbert, T, Lander, E.S., Eisenman, RN., and Golub, T R 2000. Expression analysis with oligonucleotide microarrays reveals that MYC regulates genes involved in growth, cell cycle, signaling, and adhesion. Proc Natl Acad Sci USA 97:3260-3265.
34. Bornstein, G., Bloom, J., Sitry-Shevah, D., Nakayama, K., Pagano, M., and Hershko, A 2003. Role of the SCFSkp2 ubiquitin ligase in the degradation of p21 Cip1 in S phase. J Biol Chem 278:25752-25757.
35. Abbas, T, Sivaprasad, U., Terai, K., Amador, V., Pagano, M., and Dutta, A 2008. PCNA-dependent regulation of p21 ubiquitylation and degradation via the CRL4Cdt2 ubiquitin ligase complex. Genes Dev 22:2496-2506.
36. Kim, Y., Starostina, N.G., and Kipreos, ET. 2008. The CRL4Cdt2 ubiquitin ligase targets the degradation of p21 Cip1 to control replication licensing. Genes Dev 22:2507-2519.
37. Nishitani, H., Shiomi, Y., Iida, H., Michishita, M., Takami, T, and Tsurimoto, T. 2008. CDK inhibitor p21 is degraded by a proliferating cell nuclear antigen-coupled Cu14-DDB1Cdt2 pathway during S phase and after UV irradiation. J Biol Chem 283:29045-29052.
38. Amador, V., Ge, S., Santamaria, P.G., Guardavaccaro, D., and Pagano, M. 2007. APC/C(Cdc20) controls the ubiquitin-mediated degradation of p21 in prometaphase. Mol Cell 27:462-473.
39. Lee, EW., Lee, M.S., Camus, S., Ghim, J., Yang, M. R, Oh, W., Ha, N.C., Lane, D.P., and Song, J. 2009. Differential regulation of p53 and p21 by MKRN1 E3 ligase controls cell cycle arrest and apoptosis. EMBO J. 28:2100-2113.
40. Chen, L.C., Manjeshwar, S., Lu, Y, Moore, D., Ljung, B.M., Kuo, W.L., Dairkee, S.H., Wernick, M., Collins, C., and Smith, H.S. 1998. The human homologue for the Caenorhabditis elegans cul-4 gene is amplified and overexpressed in primary breast cancers. Cancer Res 58:3677-3683.
41. Pan, H.W., Chou, H.Y., Liu, S.H., Peng, S.Y., Liu, C.L., and Hsu, H.C. 2006. Role of L2DTL, cell cycle-regulated nuclear and centrosome protein, in aggressive hepatocellular carcinoma. Cell Cycle 5:2676-2687.
42. Ueki, T, Nishidate, T, Park, J.H., Lin, M.L., Shimo, A, Hirata, K., Nakamura, Y., and Katagiri, T 2008. Involvement of elevated expression of multiple cell-cycle regulator, DTURAMP (denticleless/RA-regulated nuclear matrix associated protein), in the growth of breast cancer cells. Oncogene 27:5672-5683.
43. Yasui, K., Arii, S., Zhao, C., Imoto, I., Ueda, M., Nagai, H., Emi, M., and Inazawa, J. 2002. TFDP1, CUL4A, and CDC16 identified as targets for amplification at 13q34 in hepatocellular carcinomas. Hepatology 35: 1476-1484.
44. Martin-Caballero, J., Flores, J.M., Garcia-Palencia, P., and Serrano, M. 2001. Tumor susceptibility of p21 (Waf1/Cip1)-deficient mice. Cancer Res 61:62346238.
45. Jackson, R J., Adnane, J., Coppola, 0., Cantor, A, Sebti, S.M., and Pledger, W.J. 2002. Loss of the cell cycle inhibitors p21(Cip1) and p27(Kip1) enhances tumorigenesis in knockout mouse models. Oncogene 21: 8486-8497.
46. Poole, AJ., Heap, 0., Carroll, RE, and Tyner, AL. 2004. Tumor suppressor functions for the Cdk inhibitor p21 in the mouse colon. Oncogene 23:8128-8134.
47. Topley, G.I., Okuyama, R, Gonzales, J.G., Conti, C., and Dotto, G.P. 1999. p21(WAF1/Cip1) functions as a suppressor of malignant skin tumor formation and a determinant of keratinocyte stem-cell potential. Proc Natl Acad Sci USA 96: 9089-9094.
48. Peterson, L.F., Yan, M., and Zhang, D.E 2007. The p21Waf1 pathway is involved in blocking leukemogenesis by the t(8; 21) fusion protein AML1-ETO. Blood 109:4392-4398.
49. Barboza, J.A, Liu, G., Ju, Z., El-Nagger, AK., and Lozano, G. 2006. p21 delays tumor onset by preservation of chromosomal stability. Proc Natl Acad Sci USA 103: 19842-19847.
50. Van Nguyen, T, Puebla-Osorio, N., Pang, H., Dujka, M.E, and Zhu, C. 2007. DNA damage-induced cellular senescence is sufficient to suppress tumorigenesis: a mouse model. J Exp Med 204:1453-1461.
51. Abukhdeir, AM., and Park, B.H. 2008. P21 and p27: roles in carcinogenesis and drug resistance. Expert Rev Mol Med 10:e19.
52. Chang, B.D., Watanabe, K., Broude, EV., Fang, J., Poole, J.C., Kalinichenko, TV, and Roninson, LB. 2000. Effects of p21Waf1/Cip1/Sdi1 on cellular gene expression: implications for carcinogenesis, senescence, and age-related diseases. Proc Natl Acad Sci USA 97:4291-4296.
53. Ventura, A, Kirsch, D.G., McLaughlin, M.E., Tuveson, D.A, Grimm, J., Lintault, L., Newman, J., Reczek, EE, Weissleder, R, and Jacks, T. 2007. Restoration of p53 function leads to tumour regression in vivo. Nature 445: 661-665.
54. Wu, C.H., van Riggelen, J., Yetil, A, Fan, AC., Bachireddy, P., and Fetsher, D.W. 2007. Cellular senes- 55. Moldovan, G.L., Pfander, B., and Jentsch, S. 2007. PCNA, the maestro of the replication fork. Cell 129:665-679.
56. George, RJ., Sturmoski, M.A, May, R, Sureban, S.M., Dieckgraefe, B.K., Anant, S., and Houchen, C.W. 2009. Loss of p21Waf1/Cip1/Sdi1 enhances intestinal stem cell survival following radiation injury. Am J Physiol Gastrointest Liver Physiol 296:G245-254.
57. Deshaies, RJ., and Joazeiro, C. A 2009. RING domain E3 ubiquitin ligases. Annu Rev Biochem 78:399-434.
58. Hershko, A, and Ciechanover, A 1998. The ubiquitin system. Annu Rev Biochem 67:425-479.
59. Lightcap, E.S., McCormack, TA, Pien, C.S., Chau, V., Adams, J., and Eiiiott, P.J. 2000. Proteasome inhibition measurements: clinical application. Clin Chem 46:673-683.
60. Piva, R, Ruggeri, B., Williams, M., Costa, G., Tamagno, I., Ferrero, D., Giai, V., Coscia, M., Peola, S., Massaia, M., et al. 2008. CEP-18770: A novel, orally active proteasome inhibitor with a tumor-selective pharmacologic profile competitive with bortezomib. Blood 111:2765-2775.
61. Yang, Y., Ludwig, RL., Jensen, J.P., Pierre, S.A, Medaglia, M.v., Davydov, I.V., Safiran, Y.J., Oberoi, P., Kenten, J.H., Phillips, AC., et al. 2005. Small molecule inhibitors of HDM2 ubiquitin ligase activity stabilize and activate p53 in cells. Cancer Cell 7:547-559.
62. Shangary, S., Qin, D., McEachern, D., Liu, M., Miller, RS., Qiu, S., Nikolovska-Coleska, I., Ding, K., Wang, G., Chen, J., et al. 2008. Temporal activation of p53 by a specific MDM2 inhibitor is selectively toxic to tumors and leads to complete tumor growth inhibition. Proc Natl Acad Sci USA 105:3933-3938.
63. Vassilev, L. T, Vu, B.T, Graves, B., Carvajal, D., Podlaski, F., Filipovic, I., Kong, N., Kammlott, U., Lukacs, C., Klein, C., et al. 2004. In vivo activation of the p53 pathway by small-molecule antagonists of MDM2. Science 303:844-848.
64. Nickeleit, L, lender, S., Sasse, F., Geffers, R, Brandes, G., Sorensen, I., Steinmetz, H., Kubicka, S., Carlomagno, T, Menche, D., et al. 2008. Argyrin a reveals a critical role for the tumor suppressor protein p27(kipl) in mediating antitumor activities in response to proteasome inhibition. Cancer Cell 14:23-35.
65. Aghajan, M., Jonai, N., Flick, K., Fu, F., Luo, M., Cai, X., Ouni, I., Pierce, N., Tang, X., Lomenick, B., et al. Chemical genetics screen for enhancers of rapamycin identifies a specific inhibitor of an SCF family E3 ubiquitin ligase. Nat Biotechnol 28:738-742.
66. Orlicky, S., Tang, X., Neduva, V., Elowe, N., Brown, E.D., Sicheri, F., and Tyers, M. An allosteric inhibitor of substrate recognition by the SCF(Cdc4) ubiquitin ligase. Nat Biotechnol 28:733-737.
67. Borriello A, Caldarelli I, Bencivenga D, Criscuolo M, Cucciolla V, Tramontano A, Oliva A, Perrotta S, Della Ragione F. p57(Kip2) and cancer: time for a critical appraisal. Mol Cancer Res. 2011 October; 9(10):1269-84. Epub 2011 Aug. 4.

What is claimed is:

1. A method for determining whether a test compound inhibits the degradation of a Cip/Kip protein by the Ubiquitin-Proteasome system and may be useful for treating cancer, said method comprising
    (a) contacting said test compound with a cell expressing a fusion protein in the presence of an eukaryotic protein synthesis inhibitor, said fusion protein comprising (i) a Cip/Kip polypeptide; and (ii) a reporter protein linked to the C-terminal of said Cip/Kip polypeptide, wherein said fusion protein has a half-life that is similar to that of said Cip/Kip polypeptide, and
    (b) measuring a readout signal from the reporter protein, wherein a higher readout signal from the reporter protein in the presence of said test compound, relative to the readout signal in the absence of said test compound, is indicative that said test compound inhibits the degradation of a Cip/Kip protein by the Ubiquitin-Proteasome system and may be useful for treating cancer.

2. The method of claim 1, wherein the Cip/Kip polypeptide is a p21 polypeptide comprising the amino acid sequence of SEQ ID NO:2, or a functional variant or fragment thereof having p21 activity.

3. The method of claim 2, wherein said half-life is from 30 minutes to about 1 hour.

4. The method of claim 1, wherein said protein synthesis inhibitor is cycloheximide (CHX).

5. The method of claim 1, wherein said reporter protein is a luciferase.

6. The method of claim 5, wherein said luciferase is a *Renilla* luciferase polypeptide comprising the amino acid sequence of SEQ ID NO:4, or a functional variant or fragment thereof having *Renilla* luciferase activity.

7. The method of claim 5, wherein said readout signal from the reporter protein is bioluminescence in the presence of a luciferase substrate.

8. The method of claim 7, wherein said luciferase substrate is coelenterazine or an analog thereof.

9. The method of claim 1, wherein said cell further comprises an inducible expression system for inducible expression of the fusion protein.

10. The method of claim 9, wherein said inducible expression system is a tetracycline-controlled expression system.

11. A system for determining whether a test compound inhibits the degradation of a Cip/Kip protein by the Ubiquitin-Proteasomes system and may be useful for treating cancer, said system comprising:
    a cell expressing a fusion protein, said fusion protein comprising (i) a Cip/Kip polypeptide; and (ii) a reporter protein linked to the C-terminal of said Cip/Kip polypeptide, wherein said fusion protein has a half-life that is similar to that of said Cip/Kip polypeptide;
    an eukaryotic protein synthesis inhibitor; and
    a detection system to measure a readout signal from the reporter protein.

12. The system of claim 11, wherein the Cip/Kip polypeptide is a p21 polypeptide comprising the amino acid sequence of SEQ ID NO:2, or a functional variant or fragment thereof having p21 activity.

13. The system of claim 12, wherein said half-life is from 30 minutes to about 1 hour.

14. The system of claim 11, wherein said protein synthesis inhibitor is cycloheximide (CHX).

15. The system of claim 11, wherein said reporter protein is a luciferase.

16. The system of claim 15, wherein said luciferase is a *Renilla* luciferase polypeptide comprising the amino acid sequence of SEQ ID NO:4, or a functional variant or fragment thereof having *Renilla* luciferase activity.

17. The system of claim 15, wherein said system further comprises a luciferase substrate.

18. The system of claim 17, wherein said luciferase substrate is coelenterazine or an analog thereof.

19. The system of claim 11, wherein said cell further comprises an inducible expression system for inducible expression of the fusion protein.

20. The system of claim 19, wherein said inducible expression system is a tetracycline-controlled expression system.

* * * * *